(12) United States Patent
Dahotre et al.

(10) Patent No.: US 10,729,497 B2
(45) Date of Patent: Aug. 4, 2020

(54) LASER-ASSISTED MACHINING (LAM) OF NON-MONOLITHIC COMPOSITE BONE MATERIAL

(71) Applicant: University of North Texas, Denton, TX (US)

(72) Inventors: Narendra Dahotre, Denton, TX (US); Soundarapandian Santhanakrishnan, Madurai (IN)

(73) Assignee: UNIVERSITY OF NORTH TEXAS, Denton, TX (US)

( * ) Notice: Subject to any disclaimer, the term of this patent is extended or adjusted under 35 U.S.C. 154(b) by 42 days.

(21) Appl. No.: 16/310,917

(22) PCT Filed: Jun. 19, 2017

(86) PCT No.: PCT/US2017/038196
§ 371 (c)(1),
(2) Date: Dec. 18, 2018

(87) PCT Pub. No.: WO2017/223003
PCT Pub. Date: Dec. 28, 2017

(65) Prior Publication Data
US 2019/0142515 A1   May 16, 2019

Related U.S. Application Data

(60) Provisional application No. 62/437,167, filed on Dec. 21, 2016, provisional application No. 62/429,485, (Continued)

(51) Int. Cl.
*A61B 18/20* (2006.01)
*A61N 5/06* (2006.01)
*A61B 18/00* (2006.01)

(52) U.S. Cl.
CPC .......... *A61B 18/203* (2013.01); *A61N 5/0613* (2013.01); *A61B 2018/00565* (2013.01); (Continued)

(58) Field of Classification Search
None
See application file for complete search history.

(56) References Cited

U.S. PATENT DOCUMENTS

| 2011/0218524 | A1  | 9/2011 | Cattaneo |
| 2014/0263214 | A1* | 9/2014 | Dahotre ............... A61B 18/203 219/121.69 |

OTHER PUBLICATIONS

Notification of Transmittal of the International Preliminary Report on Patentability for PCT/US2017/038196 dated Jan. 3, 2019 from the International Bureau of WIPO, containing the Written Opinion of the International Searching Authority—European Patent Office, dated Apr. 10, 2017, 7 pages.

* cited by examiner

*Primary Examiner* — Carl H Layno
*Assistant Examiner* — Dacheng Xie
(74) *Attorney, Agent, or Firm* — Jackson Walker LLP

(57) ABSTRACT

An apparatus and method for laser-assisted machining (LAM) of non-monolithic composite bone material is described. A high intensity focused laser beam conducts bone material removal in extremely short time duration without causing any thermal (necrosis) and mechanical damage to the material surrounding the bone-laser interaction region. A computer associated with the apparatus for machining bone preferably employs a Multiphysics computational modeling approach which takes into account physical phenomena such as heat transfer, fluid flow, convection mixing, and surface tension when determining bone target volume, calculating material properties of the multicomponent and multicomposition composite bone material, deter-
(Continued)

mining parameters for the laser-assisted machining based on the material properties, and performing the laser-assisted cutting/shaping/machining of bone.

28 Claims, 27 Drawing Sheets

Related U.S. Application Data filed on Dec. 2, 2016, provisional application No. 62/352,275, filed on Jun. 20, 2016.

(52) U.S. Cl.
CPC ............... *A61B 2018/00601* (2013.01); *A61B 2018/00625* (2013.01); *A61B 2018/20553* (2017.05); *A61B 2018/205547* (2017.05)

Figure 3: Machining rates obtained during laser cutting of bone with various energy densities

FIG. 8A

| Boundary Number | Boundary Conditions | Equation |
|---|---|---|
| Whole geometry | Governing equation | $\rho C_p \left[\dfrac{\partial T}{\partial t}\right] = k\left[\left(\dfrac{\partial^2 T}{\partial x^2}\right) + \left(\dfrac{\partial^2 T}{\partial y^2}\right)\right]$ |
| 6 | Heat flux, natural convection cooling and radiation | $-k\dfrac{\partial T}{\partial y} = \varphi P_x - h[T - T_i] - \varepsilon\sigma[T^4 - T_i^4]$<br>Where, $\varphi = 1$ for $0 \le t \le t_r$, and $\varphi = $ for $t \ge t_r$ |
|  | Average laser power density in Gaussian distribution<br>Or<br>Average laser power density in Top hat distribution<br>Or<br>Average laser power density in Dumbbell distribution | $P_g = \dfrac{P_0}{\pi r_0^2} exp\left[-\left[\dfrac{x^2+y^2}{r_0^2}\right]\right]$<br><br>$P_{th} = \dfrac{P_0}{\pi r_0^2} exp\left[-\left[\dfrac{x^2+y^2}{r_0^2}\right]^n\right]$ (where $n \to \infty$)<br><br>$P_{db} = \dfrac{2P_0}{\pi r_0^2}\left(\dfrac{x}{r_0}\right)^2 exp\left[-\left[\dfrac{x^2+y^2}{r_0^2}\right]^2\right]$ |
| 1, 9 | Natural convection cooling and radiation | $-k\dfrac{\partial T}{\partial x} = h[T - T_i] - \varepsilon\sigma[T^4 - T_i^4]$ |
| 3, 8 | Natural convection cooling and radiation | $-k\dfrac{\partial T}{\partial y} = h[T - T_i] - \varepsilon\sigma[T^4 - T_i^4]$ |
| 2 | Insulation | $\dfrac{\partial T}{\partial y} = 0$ |

FIG. 9A

| Ex # | Laser power (W) | Scanning speed (m/s) | Residence time (ms)* | Laser Energy Density ($\times 10^6$ J/m$^2$)** | Laser Machining Attributes ||||| Machining Rate (m$^3$/s) | Machining Rate*** (m$^3$/s/W) Or (m$^3$/J) $\times 10^{-2}$ |
|---|---|---|---|---|---|---|---|---|---|---|
| | | | | | Measured Experimentally || Determined Computationally || | |
| | | | | | Depth (μm) | Width (μm) | Depth (μm) | Width (μm) | | |
| 1 | 300 | 0.2  | 3.0 | 3.18 | 140 | 300 | 105 | 265 | 3.3  | 1.1 |
| 2 | 400 | 0.2  | 3.0 | 4.24 | 190 | 360 | 185 | 330 | 6.4  | 1.6 |
| 3 | 550 | 0.25 | 2.4 | 4.67 | 250 | 410 | 225 | 375 | 14.4 | 2.6 |
| 4 | 500 | 0.2  | 3.0 | 5.31 | 330 | 470 | 295 | 430 | 19.1 | 3.8 |
| 5 | 450 | 0.15 | 4.0 | 6.36 | 410 | 530 | 430 | 535 | 22.6 | 5.0 |
| 6 | 600 | 0.2  | 3.0 | 6.40 | 430 | 540 | 445 | 550 | 32.8 | 5.5 |
| 7 | 700 | 0.2  | 3.0 | 7.43 | 590 | 650 | 610 | 690 | 65.2 | 9.3 |
| 8 | 400 | 0.1  | 6.0 | 8.49 | 730 | 800 | 780 | 810 | 61.1 | 15.3 |

\* Residence time (s) = Laser beam diameter (m)/scanning speed (m/s)
\*\* Laser energy density (J/m$^2$) = (Laser power (J/s)/laser irradiation area (m$^2$)) × (laser beam diameter (m)/scanning speed (m/s))
\*\*\* Machining rate (m$^3$/Js) = Volume of material removed (m$^3$)/residence time (s)/laser energy density (J/m$^2$)

Fig 2. Scanning electron microscopy top view of laser machined cavity in structural bone with various machining parameters.

Fig 3. Scanning electron microscopy cross sectioal view of laser machined cavity in structural bone with various machining parameters.

Fig 4. Scanning electron microscopy view of laser machined bone sample at 5.30 J/mm² laser energy density showing various machined regions and corresponding elemental composition within these regions. Region 1: Base bone material; Region 2: Heat affected zone surrounding machined region; and Region 3: Machined bone region.

FIG. 17

Table 3: Experimental estimates and computational predictions of attributes of laser bone machined cavity

| Laser Fluence (J/mm²) | Remarks | Equivalent Linear Force (J/mm or ×10⁻³N) | Experimental | | | | | Computational | | | |
|---|---|---|---|---|---|---|---|---|---|---|---|
| | | | Depth (μm) | Width (μm) | $R_E = \frac{Depth}{Width}$ | Area (μm²) | Machining Rate (mm³/s) | Depth (μm) | Width (μm) | $R_C = \frac{Depth}{Width}$ | Area (μm²) | Machining Rate (mm³/s) |
| 3.18 | Group 1 Constant Scanning Speed and Variable Power | 1.5 | 136 ± 5 | 293 ± 6 | 0.46 ± 0.8 | 39964 ± 32 | 8 ± 0.3 | 203 | 421 | 0.48 | 67238 | 13.4 |
| 4.24 | | 2.0 | 186 ± 6 | 409 ± 2 | 0.45 ± 4.0 | 75978 ± 9 | 15 ± 0.4 | 225 | 432 | 0.52 | 76421 | 15.3 |
| 5.30 | | 2.5 | 365 ± 10 | 718 ± 14 | 0.51 ± 0.7 | 262028 ± 126 | 52 ± 1.3 | 370 | 749 | 0.49 | 218032 | 43.6 |
| 6.36 | | 3.0 | 400 ± 9 | 829 ± 6 | 0.48 ± 1.5 | 381741 ± 58 | 76 ± 1.5 | 465 | 929 | 0.50 | 340230 | 68 |
| 7.42 | | 3.5 | 822 ± 4 | 688 ± 10 | 1.19 ± 0.4 | 565814 ± 42 | 113 ± 0.6 | 516 | 990 | 0.52 | 401903 | 80.3 |
| 3.18 | Group 2 Variable Scanning Speed and Variable Power | 1.5 | 136 ± 5 | 293 ± 6 | 0.46 ± 0.8 | 39964 ± 32 | 8 ± 0.3 | 203 | 421 | 0.48 | 67238 | 13.4 |
| 4.66 | | 2.2 | 255 ± 7 | 436 ± 8 | 0.58 ± 0.9 | 111486 ± 31 | 29 ± 0.7 | 360 | 800 | 0.45 | 226584 | 56.6 |
| 6.36 | | 3.0 | 428 ± 10 | 843 ± 6 | 0.51 ± 5 | 360963 ± 56 | 54 ± 1.2 | 440 | 950 | 0.46 | 328861 | 49.3 |
| 8.38 | | 4.0 | 737 ± 23 | 935 ± 20 | 0.79 ± 5 | 689409 ± 67 | 69 ± 0.3 | 503 | 1014 | 0.56 | 402371 | 40.3 |

Fig 8. Thermal fields at various depths below surface and corresponding evolution of machined cavity in laser machined structural bone

LASER-ASSISTED MACHINING (LAM) OF NON-MONOLITHIC COMPOSITE BONE MATERIAL

This application claims priority to U.S. Provisional Patent Application Ser. No. 62/352,275, filed on Jun. 20, 2016, U.S. Provisional Patent Application Ser. No. 62/429,485, filed on Dec. 2, 2016, and U.S. Provisional Patent Application Ser. No. 62/437,167, filed on Dec. 21, 2016, each entitled "Laser-Assisted Machining (LAM) of Non-Monolithic Composite Bone Material," and the contents of each are hereby incorporated by reference in their entireties.

BACKGROUND

The present invention relates generally to a system and methods of cutting/shaping/machining bone material, taking into account its non-monolithic, composite nature, and more specifically to a system for the process and apparatus for laser assisted machining ("LAM") of bone.

The cutting process forms one of the important bone shaping operations during orthopaedic surgeries. Today, although the orthopaedic surgery has come a long way through adaptation/integration of modern tools such as sensors and CAD (computer aided drawing) based generation of patient specific defined joint design and bone shaping/cutting parameters, it is still largely conducted by the surgeon using conventional tools such as saw, ultrasonic cutter, hammer, drill, etc. Such mostly conventional way of surgery is associated with human and tool attributes that mostly result in potentially increasing the risk of thermal damage (necrosis). This situation in turn leaves tremendous room for further development of operating tools and techniques. These further developments are likely to address several additional collateral adverse effects of orthopaedic surgery such as but not limited to (1) severe damage of tissues within and surrounding repaired/operated regions, (2) low precision in final dimensional tolerance on repaired/operated bone, (3) relatively slow surgical processes, (4) post-surgery tissue trauma, (5) rigorous pain, and (6) in some cases, post-surgery and related addition of cost.

Cutting saws and burrs are the traditional tools employed for bone cutting during orthopaedic surgery. Being a manual operation, it involves human errors and necessity of skilled surgeons thus making achievement of reproducibility difficult. Apart from these variabilities, there are other issues associated, such as thermally driven necrosis of tissues initiated by temperature rise due to extended period physical contact between the cutting/shaping tool and bone that leads to friction/abrasion between cutting tool and bone, along with heavy mechanical loading of bones during conventional mechanical cutting/shaping/machining. In general, cutting saw blades are much harsher than cutting burrs, with temperatures of bone rising above 100° C. The reason behind this increase in temperature is the large contact area of bone with the saw teeth. In addition, there are many cuts that need to be performed in order to shape the bone. Although the cutting operation using burr results in moderate temperatures (50-60° C.), burr cutting is limited to shallow cuts, thus not a complete substitute for the cutting saw.

To address the temperature rise, and avoid associated necrosis, many remedies have been explored that are mainly focused on (a) change in tool design, (b) improving method of operation and most prevalent (c) employing saline cooling. Out of these, (a), and (b) still require careful operational procedures to achieve lower heat generation. In case of (c), even though the temperature rise can be controlled, designing an effective cooling system becomes necessary. For cutting tools, internally cooled tools have been reported to be superior in terms of heat control than an external spray/mist cooling. Intricately designed tools and careful temperature and flow rate control are required to achieve low heat generation. Furthermore, due to the physical contact between the mechanical cutting tools and bone, a very cautious sterilization process for tools is required to avoid any risk of infection. Apart from these issues, the conventional bone cutting/shaping/machining also involves post tissue trauma and rigorous pain and long healing/recovery times.

Furthermore, as a result of the composite nature of the bone, the direction of mechanical loading during cutting critically determines the response of bone to cutting. Factors such as porosity, mineralization, and orientation-diameter-spacing of collagen fibers of histological structure of bone play a deterministic role in mechanical response. It has been well documented in the literature that the mechanical response changes drastically depending upon the orientation of these microstructural features with the loading direction. Thus anisotropy and heterogeneity of bone structure makes it difficult to predict the exact response of bone to cutting operation as well as leads to uneven site specific stress concentration and generation of microcracks and/or cracks. This situation also further leads to unpredictable fracture of the bone in ductile or brittle or mixed (ductile+brittle) manner that in turn leads to unpredictable cut surface quality (roughness) which holds tremendous bearing on post-surgery bone ingrowth and healing characteristics. In light of this situation it is extremely difficult to design/select cutting parameters (speed, force, feed rate) and cutting saw parameters (tooth spacing or pitch, tooth size, tooth form) for desired outcome and mostly remains an art related to skill and experience of the surgeon.

SUMMARY

The present disclosure relates to a non-conventional laser-based non-contact technique for cutting, shaping, and machining bone. The current method takes a radically different approach to achieve superior cutting/shaping/machining operation. It is based on employment of extremely short duration non-physical contact high intensity laser beam as the energy source for cutting/shaping/machining. Such high intensity focused laser beam conducts bone material removal in extremely short time duration without causing any thermal (necrosis) and mechanical damage to the material surrounding the bone-laser interaction region. Furthermore, the laser based bone cutting/shaping/machining technique is highly amenable to automation and reduction in human intervention and operation time along with increasing precision in cutting/shaping/machining. These primary advantages are expected to lead to secondary benefits such as rapid patient recovery and reduction in cost.

It is evident that conventional cutting techniques, in spite of having short comings, are still in use. The efforts to improve this operation need to eliminate (a) complex system arrangements, (b) variabilities introduced by human factor, and (c) physical contact between the cutting/shaping tool and bone. In light of this, the present novel and non-conventional laser based non-contact technique for shaping/cutting bone was developed. The technique is based on employment of extremely short duration non-physical contact high intensity laser beam as the energy source for shaping/cutting. Such high intensity focused laser beam allows bone material removal in extremely short time duration. The use of a laser, in general, wields inherent advantages over the conventional mechanical shaping/cutting methods such as but not limited to (a) high control over processing parameters, (b) high precision and repeatability in operation, (b) highly confined/localized heating for minimal thermal damage in surrounding volume of material, and (d) high speed shaping/cutting operation. Furthermore, the laser based shaping/cutting method being a non-contact method, it eliminates risk of mechanical loading and is more likely to eliminate or substantially reduce associated undesired effects such as cracking of bone material. Furthermore, such novel laser based bone shaping/cutting technique is highly amenable to automation and reduction in human intervention and operation time along with increasing precision in shaping/cutting. In addition, these primary advantages are expected to lead to secondary benefits such as rapid patient recovery and reduction in cost.

Lasers have been previously explored for bone (hard tissue) ablation purposes. Most of these studies were confined to evaluation of parametric correlations between laser parameters and resultant morphology of ablated surface (depth of ablation) and ablation rate (machining rate) along with study of thermal effects (necrosis and microcracks). Furthermore, some of these studies involved machined hard tissues such as monolithic dental enamel and, although associated with non-thermal (cold ablation) without collateral damage to the tissue, they produced very shallow depth ($\leq 1$ µm) and/or low machining rates (<1 mm$^3$/s) due to use of ultrashort pulse fs or ps lasers. Remaining studies, though they employed continuous wave (CW) and pulsed $CO_2$ Nd:YAG, Ho:YAG, and Er:YAG lasers for machining of non-monolithic structural bones, were confined to only shallow drilling and cutting (<2 mm depth) operations and observations indicated substantial necrosis of the bone around the cut region and appeared to generate very low machining rates (1 mm$^3$/s). On the contrary, in case of orthopaedic surgeries for hard tissue bio implant replacement (knee, hip, etc), higher machining rates ($\geq 30$ mm$^3$/s) with minimal collateral thermal damage to the structural bone is desired.

The use of lasers, in general, wields inherent advantages over the conventional mechanical cutting/shaping/machining methods such as but not limited to (a) high control over processing parameters, (b) high precision and repeatability in operation, (c) highly confined/localized heating for minimal thermal damage in surrounding volume of material, and (d) high speed cutting/shaping/machining operation. Furthermore, because the laser based cutting/shaping/machining method is a non-contact method, it eliminates the risks of mechanical loading and associated undesired effects such as cracking of bone material. It is worth noting that, a laser being an intense heat source, in laser based operation, heat is not a byproduct but a vehicle for material removal. Due to its high intensity (energy density), material within the laser-material interaction region is removed by instantaneously raising its temperature to melting and/or vaporization temperature with minimally or without thermally affecting the surrounding region. Based on these advantages, lasers have been previously explored for bone ablation purposes.

Bone material removal by laser is challenging due to the diverse thermophysical properties of the bone constituents. The mineral (hydroxyapatite) has a high melting point (about 1100° C.) whereas organic matrix consisting of collagen experiences the onset of necrosis at ~45° C. and completely carbonizes at >100° C. after evaporation of water. Water plays a critical role in determining the ablation mechanism depending on the wavelength of the laser used. Some of the wavelengths are strongly absorbed by the water making it to quickly boil, while others are transmitted through it creating a possibility of damaging the tissues underneath. Copper vapor laser (wavelength=511 nm) and Nd:YAG laser operating at 532 nm are easily transmitted through water. On the other hand, Er:YAG laser (wavelength=2.940 µm) and Nd:YAG laser operated at 2900 nm wavelength are strongly absorbed by water. Other lasers absorbed by water are $CO_2$ lasers (wavelength=10.6 µm), Yb-fiber laser (wavelength=1.07 µm), and Nd:YAG laser operated at wavelength of 1.06 µm.

Ablation mechanism is critically influenced by the time of interaction and power density. For exposures greater than 1 s, the laser is preferably operated in a continuous wave mode giving rise to photochemical interactions. The time range of 1 min to 1 µs gives rise to thermal interactions. Often for the shorter interaction times, the laser operates in a pulse mode. The exposure time in the range of 1 µs to 1 ns results in photoablation. Extremely short exposure durations of the order <1 ns give rise to plasma-induced ablation and photodisruption.

In preferred embodiments of the current methods and systems, Yb-fiber coupled Nd:YAG laser (1.07 µm wavelength) is used to machine a structural bone. Evaluation focused on a fundamental/basic understanding of laser interaction with bone material system. Such basic evaluation was attempted with integrated experimental and computational approach for optimization of the laser process parameters to achieve most effective removal/ablation (shaping/cutting) of the bone with least possible thermal damage.

The heat transfer model extends to multi-pass laser processing for larger area and larger volume material removal (cutting/shaping/machining) and the laser processing is optimized by a modeling approach to consider the reheating effects. The level-set method is specifically employed to predict the evolution of solid-liquid-vapor interface. Temporal tracking of such interface predicts the volume of portion of substrate melted and/or vaporized and in turn aids to estimate the geometrical dimensions of cut/shaped/machined volume (depth and width) during laser cutting/shaping/machining of bone.

Furthermore, the present computational model incorporates the heat transfer, fluid flow, and structural mechanics boundary conditions corresponding to various physical phenomena (Marangoni convection, surface tension, recoil pressure, and structural deformation) and temperature-dependent bone material properties (thermal conductivity, heat capacity, elastic modulus, coefficient of thermal expansion, and dynamic viscosity) in order to assess the temperature (T) profile, associated cooling rate, subsequent surface topography of cut/shaped/machined region, and resultant thermal stresses in the surrounding region during multidimensional laser cutting/shaping/machining. Also for higher accuracy and more realistic computational predictions, the temperature dependent thermophysical properties of the bone are considered. In order to address the multicomponent and multicompositional nature of bone, any thermophysical and/or themomechanical property ($M_{bone}$) of bone is estimated using the thermophysical and/or thermomechanical properties $M_{mineral}$, $M_{water}$, $M_{collagen}$, and $M_{porosity}$ of the individual components mineral (hydroxyapatite), water, collagen, and porosity respectively of the bone following rule of mixture:

$$M_{bone} = (X_{mineral} * M_{mineral}) + (X_{water} * M_{water}) + (X_{collagen} * M_{collagen}) + (X_{porosity} * M_{porosity}) \quad (7)$$

where $X_{mineral}$, $X_{water}$, $X_{collagen}$, $X_{porosity}$ are the volume fractions of mineral, water, collagen, and porosity respectively.

Due to the rapid rise in temperature (up to vaporization temperature) in laser bone-material interaction region, the surrounding region may experience steep thermal gradient, thereby leading to generation of fracture cracks. To avoid generation of thermal stress cracking via design of laser processing parameters based on computationally predicted thermal fields, the model couples solid mechanics interface with a heat transfer interface in such a way that the thermal field from heat transfer interface acts as a thermal load for the solid mechanics interface. The temperature-dependent elastic modulus and coefficient of thermal expansion are assigned to the model to effectively incorporate elastic behavior law. The temperature history evaluated from the present multiphysics model is used as input to the thermal stress analysis, which in turn is modeled as elastic-plastic material with isotropic hardening and temperature dependent yield stress.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8A shows governing equations for a computational model used in accordance with exemplary embodiments of the present disclosure to represent temperature-dependent material properties of a region of bone.

FIG. 9A shows a table of bone tissue cutting/shaping/machining rate as a function of laser energy density in accordance with exemplary embodiments of the present disclosure.

FIG. 17 shows a table with experimental estimates and computational predictions of attributes of a laser bone machined cavity.

DETAILED DESCRIPTION

Figure 1:
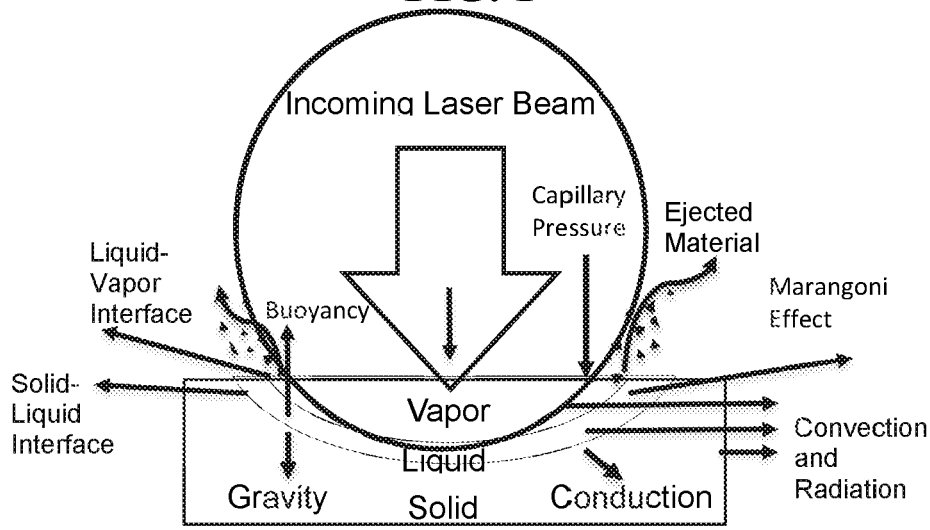
FIG. 1 shows a schematic illustration of combinatorial effects of physical phenomena on evolution of physical attributes/surface topography (depth, width, and geometry) of a cut/shaped/machined region of hard tissue or bone and thermal stresses in the surrounding region.

The present disclosure pertains to methods and apparatus for laser-assisted machining of bone. In preferred embodiments, the laser-assisted machining of bone utilizes a multiphysics computational model approach that takes into account the fact that biological hard tissue/bone is a non-monolithic multicomponent (ceramic+collagen+water+porosity) material system.

The current disclosure pertains to methods and apparatus for laser-assisted machining of bone, taking into account its non-monolithic, composite (multicomponent and multicomposition) nature. In preferred embodiments, the method includes a step of determining a bone target volume or target area to be machined. Once the bone target volume has been determined, a focused laser beam will be used to scan the laser along a surface area axis of the bone's target volume at a calculated machining-rate. The method utilizes a Gaussian shaped, or top-hat, or dumbbell laser beam profile for the bone target. The focused laser beam will generate intense heat, which will instantaneously evaporate the liquid layer and other organic (collagen) and inorganic/mineral/ceramic (hydroxyapatite) components of the bone thereby ejecting a bone residue from the predetermined target bone volume creating a cut/shaped/machined void in the bone.

The machining rate of the bone is determined from calculations using cutting/shaping/machining parameters such as: laser power output; the target bone volume; the diameter of the focused laser beam; the laser scanning speed; and the residence time. The laser energy density provides a narrow laser beam with a high power density with little or no heat affected zones ("HAZ") on the bone targeted volume.

In preferred embodiments the choice of lasers used can be selected from those that generate the focused laser beam having the laser energy density in the range of 2.0 to $12.0 \times 10^6$ J/m². Additionally, the focused laser beam preferably has a wavelength in the range of 300 nm to 29,400 nm. Lasers are preferably chosen from: a Ti-Sapphire laser, a $CO_2$ laser, an Excimer laser, a YAG laser, an Er-YAG laser, a copper vapor laser, or a Yb-fiber laser. The laser may be operated in pulse mode or continuous mode in additional preferred embodiments. The pulse mode operation of the laser allows tailoring of the pulse for desired parameters (e.g., pulse frequency, pulse shape, and pulse energy distribution) with better control of input energy in spatial (Gaussian, top hat, and dumbbell) and temporal manners for enhanced machining characteristics. In addition, a preferred beam diameter or focal spot diameter may range from 0.3 mm to 3.0 mm. In addition, in a further preferred embodiment, a laser may be utilized having a resident time in the range of 0.5 μs to 4 ms. These parameters provide high levels of control during machining and higher dimensional accuracy and speed. The focused laser beam may generate a heat intensity in the range of $4.2\text{-}9.9 \times 10^7$ W/m².

Additional embodiments may include a vision system (i.e. ScanLab) and a computer numeric controlled ("CNC") robotic system that are integrated with the laser for full automation of selecting the bone target volume and scanning the focused laser beam along a surface area axis of bone target volume at a machining rate. Further embodiments may include an apparatus for machining bone, comprising a laser source capable of delivering a focused laser beam, a dynamic focusing unit for delivering the focused laser beam to a visualized target site, and a real time controller ("RTC") capable of simultaneous processing of visualized target site data and controlling the laser source and controlling the dynamic focusing unit, wherein the RTC is able to correct laser source output for the purpose of preventing heat affected zones in the bone target and machining bone in a predetermined pattern.

Further embodiments may pertain to a process for laser-assisted machining of bone. This process may include the steps of observing a region of bone to be cut/shaped/machined, calculating the temperature-dependent material properties of the region of bone, determining parameters for laser-assisted machining based on the temperature-dependent material properties of the region of bone, and performing laser-assisted bone machining using the determined parameters.

In certain preferred embodiments, a computer associated with the apparatus for cutting/shaping/machining bone will employ a multiphysics computational modeling approach which takes into account physical phenomena such as heat transfer, fluid flow, convection mixing, and surface tension when determining bone target volume, calculating material properties of the composite bone material, determining parameters for the laser-assisted machining based on the material properties, and performing the laser-assisted machining of bone.

It is extremely important to control the thermodynamic and kinetic conditions during laser cutting/shaping/machining as the process involves removal of molten and/or vaporized material. The level of temperature developed within laser-material (biological hard tissue/bone) interaction region will define the heating and cooling rates (heat transfer) and also the mode of material removal (mass transfer). These thermodynamic and kinetic conditions and associated thermodynamic phenomena have enormous influence on the evolution of various attributes of the cutting/shaping/machining of biological hard tissue/bone such as composition, thermal stresses in machined region, machined surface morphology (roughness), microstructure, and physical defects (porosity, cracking) in cut/shaped/machined surface region and cutting/shaping/machining rate. As in case of biological hard tissue/bone, compositional changes, excessive thermal/residual stress (equal or higher than fracture stress), and porosity cause deterioration of mechanical and chemical properties, so it is extremely important to avoid generation of thermodynamic and kinetic conditions leading to these attributes. Similarly for any technical application, the practical aspects of cutting/shaping/machining such as cut/shaped/machined surface morphology (roughness) and cutting/shaping/machining rate are also very important. Hence, while avoiding generation of undesirable attributes, it is also important to control the evolution of desirable attributes by precise control over thermodynamic and kinetic conditions during laser cutting/shaping/machining of biological hard tissue/bone. Therefore, the thermodynamic and kinetic conditions required to achieve the desired attributes can be achieved through an integrated computational modeling and experimental approach.

Computational modeling forms an important facet of the current laser-based cutting/shaping/machining method. Considering the dynamic nature of the laser cutting/shaping/machining consisting of very short interaction times ranging from milli- to pico-seconds, it is extremely difficult to capture/realize various physical phenomena via measurement of thermodynamic and kinetic parameters during the process. In view of this, a multiphysics computational modeling approach incorporating physical phenomena such as heat transfer, fluid flow, convection mixing, surface tension, and the like can be utilized. Through understanding of correlation among these physical phenomena, the next level of correlation between these physical phenomena and laser processing parameters provides better control of laser ablation/removal (cutting/shaping/machining rate) and evolution of physical attributes (cut/shaped/machined geometry) during bone cutting/shaping/machining operation. Furthermore, this methodology can be extended to optimization (analysis of variance—ANOVA) to achieve higher processing efficiency.

During multidimensional laser cutting/shaping/machining, material experiences various physical phenomena such as phase transition from solid-to-liquid-to-vapor and material loss during evaporation. In addition, the material surrounding the cut/machined/ablated region also experiences the transition dependent effects such as thermal expansion during heating, recoil pressure during vaporization, and Marangoni convection and surface tension during solidification. In order to take into account such complex laser cutting/shaping/machining mechanisms, the present model uses multistep multiphysics computational modeling approach for multidimensional (1-, 2-, and 3D) laser cutting/shaping/machining process on a multiphysics finite-element platform. The computational model based on the multiphysics approach combines heat transfer, fluid flow, and structural mechanics for thermo-mechanical coupling (temperature and thermal expansion coefficient) to investigate the combinatorial effects of these physical phenomena on evolution of physical attributes/surface topography (depth, width, and geometry) of cut/shaped/machined region and thermal stresses in the surrounding region as schematically presented in FIG. 1. The selective governing equations and boundary conditions for a multiphysics computational model are presented below.

The cooling rates and temperature evolution are determined by the solution of the equation governing the heat transfer shown below:

$$\rho C_p \frac{\partial T(x, y, z, t)}{\partial t} = k\left[\left(\frac{\partial^2 T(x, y, z, t)}{\partial x^2}\right) + \left(\frac{\partial^2 T(x, y, z, t)}{\partial y^2}\right) + \left(\frac{\partial^2 T(x, y, z, t)}{\partial z^2}\right)\right]$$

Here, k is the thermal conductivity, $C_p$ is the specific heat and $\rho$ is the density of the material. The laser track is assigned a heat flux boundary with a moving laser beam defined by the equation below:

$$-k\left[\left(\frac{\partial T}{\partial x}\right) + \left(\frac{\partial T}{\partial y}\right) + \left(\frac{\partial T}{\partial z}\right)\right] = P_X + h[T - T_0] + \varepsilon\sigma[T^4 - T_0^4]$$

Here, h is heat transfer coefficient, c is emissivity, $\sigma$ is Stefan-Boltzman constant, $T_0$ is ambient temperature, and $P_X$ is the input laser power intensity distribution and it is either $P_g$ or $P_{th}$ or $P_{db}$ where $P_g$ is the three dimensional Gaussian laser beam power intensity distribution, $P_{th}$ is the top hat laser beam power intensity distribution, and $P_{db}$ is the dumbbell laser beam power intensity distribution. The moving laser beam with a Gaussian, top hat, and dumbbell power intensity distributions are expressed below by the respective equations:

$$P_g = \frac{P_0}{\pi r_0^2} \exp\left[-\left[\frac{x^2+y^2}{r_0^2}\right]^2\right]$$

$$P_{th} = \frac{P_0}{\pi r_0^2} \exp\left[-\left[\frac{x^2+y^2}{r_0^2}\right]^n\right]$$

(where $n \to \infty$)

$$P_{db} = \frac{P_0}{\pi r_0^2}\left(\frac{x}{r_0}\right)^2 \exp\left[-\left[\frac{x^2+y^2}{r_0^2}\right]^2\right]$$

(see Koechner 2005, Willstrand 2013) where $P_0$ is laser input power, $r_0$ is the radius of beam at which laser power transverse intensity decreases to $1/e^2$, and x, y, z are the Cartesian coordinates with y along the axis of the beam and x and z are in the plane orthogonal to the axis of the beam and the beam intensity distribution is considered axisymmetric in x-z plane.

In additional preferred embodiments, the laser track is assigned a heat flux boundary with a moving laser beam defined by the equation below:

$$-k\left[\left(\frac{\partial T}{\partial x}\right) + \left(\frac{\partial T}{\partial y}\right) + \left(\frac{\partial T}{\partial z}\right)\right] = -P_g + h[T - T_0] + \varepsilon\sigma[T^4 - T_0^4]$$

Here, h is heat transfer coefficient, $\varepsilon$ is emissivity, $P_g$ is the three-dimensional Gaussian laser beam distribution, $\sigma$ is Stefan-Boltzman constant, and $T_0$ is ambient temperature.

Two important aspects of laser-material interaction that strongly influence the heat transfer and fluid flow and hence morphological (width and depth) and topographical (roughness) evolutions in machined sample are energy distribution within the laser beam and recoil pressure generated by the surface tension and/or vaporized material. The inherently fundamental Gaussian energy distribution, $P_g$ within the moving beam and the corresponding recoil pressure, $P_r$ are given by the equations below, respectively:

$$P_t = (P/(\tfrac{\pi}{4}D^2))\exp\left(-\frac{(x - V_{in} * t)^2}{(2\phi^2)}\right)$$

$$P_r = (P_g)\frac{1.69}{\sqrt{L_v}}\left[\frac{\sqrt{\left(\frac{k \cdot T_s}{M_v \cdot L_v}\right)}}{1 + 2.2\left(\frac{k \cdot T_s}{M_v \cdot L_v}\right)^2}\right] \text{ only when } T_s \geq T_v$$

where P is laser power, x is the distance along the x-axis and $\phi$ represents the standard deviation of laser beam intensity. $L_v$ is latent heat of vaporization; $M_v$ mass of vapor molecule; and $T_s$ and $T_v$ are instantaneous surface and vaporization temperatures respectively.

All other surfaces are assigned convective cooling and surface to ambient radiation boundary conditions given by the following relationship:

$$-k\left[\left(\frac{\partial T}{\partial x}\right) + \left(\frac{\partial T}{\partial y}\right) + \left(\frac{\partial T}{\partial z}\right)\right] = h[T - T_0] + \varepsilon\sigma[T^4 - T_0^4]$$

Although in the present efforts, only single laser track machining under various set of laser processing parameters was performed, the present heat transfer model can be extended to multi-pass laser processing with consideration to the reheating effects that would be required to machine a large area/volume bone material removal (machining) during any orthopaedic surgery. Furthermore, the level-set method can be specifically employed to predict/track the evolution of solid-liquid-vapor interface. Temporal tracking of such interface predicts the volume of portion of substrate bone melted and/or vaporized and in turn it assists in estimation of the geometrical dimensions of machined region (depth and width) during laser machining of bone.

Furthermore, the present computational model incorporates the heat transfer, fluid flow, and structural mechanics boundary conditions corresponding to various physical phenomena (Marangoni convection, surface tension, recoil pressure, and structural deformation) and bone material properties (thermal conductivity, heat capacity, elastic modulus, coefficient of thermal expansion, and dynamic viscosity) in order to assess the temperature (T) profile, associated heating/cooling rate, subsequent surface topography of machined region during multidimensional laser machining. Due to the paucity of data in the open literature related to above mentioned thermo-physical properties of bone, only their constant values mostly at room temperature were considered. However, in order to address the multi-component nature of bone (60-70% hydroxyapatite, 10-30% collagen, and 10-20% water by volume) average thermosphysical properties of bone were estimated using the rule of mixture and presented in Table 1.

TABLE 1

| Property | Value for Individual Component | | | Rule of Mixture Value |
| --- | --- | --- | --- | --- |
| | Mineral (Hydroxypatite) | Collagen | Water | |
| Density (Kg/cm$^3$) | 3140-3210 | 1000 | 1000 | 2413.75 |
| Thermal Conductivity (W/m$^2$/K) | 0.373-0.496 | 0.55 | 0.60 | 0.4824 |
| Specific Heat (J/g/K) | 0.662 | 1.79 | 4.17 | 1.414 |
| Emissivity | | 1.01 | | |

In preferred embodiments, laser interaction with substrate material during machining leads to evolution of surface topography due to rise in the laser-material interaction region leading to melting and vaporization of the region. The changes in temperatures within this region are represented by isotherms predicted using finite element based multiphysics model involving the equations described above. The computational model based predicted isotherms corresponding to the interfaces between solid substrate-melt zone and melt zone-vaporized region clearly define surface topography evolved during cutting/shaping/machining process. Thus the morphology of final cut/shaped/machined region can be precisely predicted/controlled by controlling spatial and temporal thermal conditions (laser machining parameters) for generation and removal of melt and vaporized volumes of the substrate material from the laser-material interaction region based on the multiphysics model involving the equations above.

Figure 2:
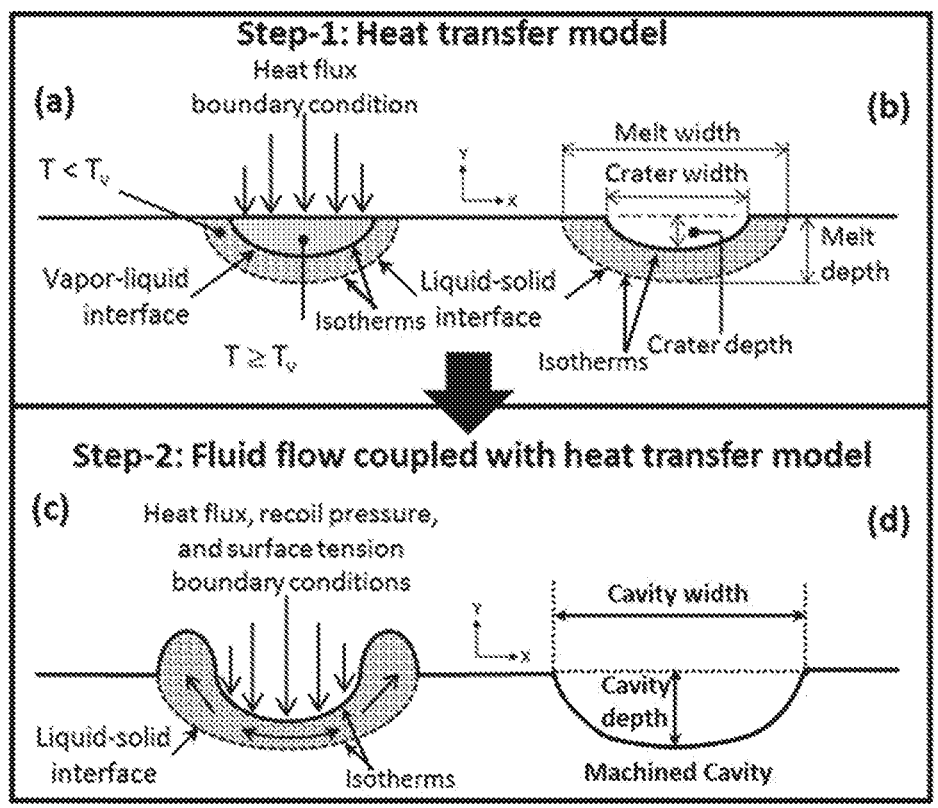
FIG. 2 shows a schematic illustration of two-step heat transfer model coupled with fluid flow model in a computational approach for determination of attributes of a laser cut/shaped/machined cavity in accordance with exemplary embodiments of the present disclosure.

Further, embodiments pertain to computational prediction of evolution of the final morphology (geometrical attributes such as width and depth) of the cut/shaped/machined cavity via adoption of a two-step computational heat transfer model coupled with a fluid flow model as schematically presented in FIG. 2. During cutting/shaping/machining process, as the temperature rises, material changes its phase from solid to liquid to vapor. The top portion of material that attains the temperature above vaporization temperature is consequently removed due to vaporization and vapor recoil pressure. The portion below vaporized region (molten region) is at the melting temperature that under the dynamic forces (recoil pressure, convectional force, gravitational force, surface tension and the like) experiences partial to complete ejection (depending upon the magnitude of these forces) and physical deformation before solidification (during cooling) and this together with vaporized region generates the final attributes (width and depth) of cut/shaped/machined cavity.

Figure 3:
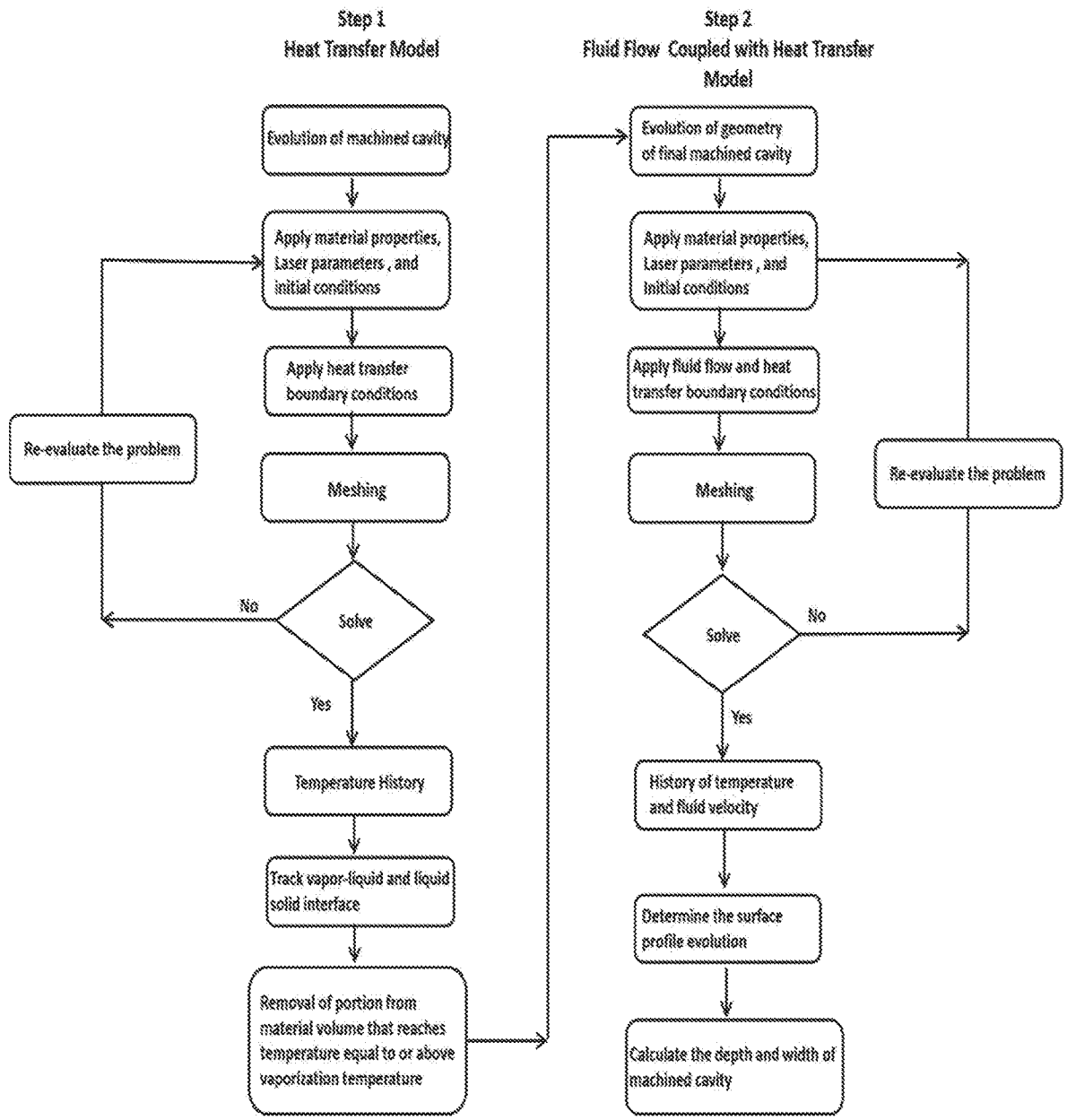
FIG. 3 shows a loop diagram of an integrated approach for prediction of morphology of a final cut/shaped/machined cavity using heat transfer and fluid flow coupled models in accordance with exemplary embodiments of the present disclosure.

Preferred embodiments of the present multiphysics computational model utilize a two-step approach for multidimensional laser cutting/shaping/machining processes for bone. An integrated approach for prediction of morphology of the final cut/shaped/machined cavity using heat transfer and fluid flow coupled models based on the equations is presented in the loop diagram of FIG. 3. In these embodiments, Step 1 of the computational model (coupled with heat transfer, structural mechanics, and phase change kinetics) predicts the geometry of a cut/ablated crater produced via evaporation losses of the material. In Step 1, the level-set method will be employed to trace the interfaces between liquid-solid and vapor-liquid phases so that the elements whose temperature reaches above the vaporization temperature are excluded from the geometry. The dimensions of cut/shaped/machined cavity (depth and width) play a significant role in predicting the final surface profile and associated thermal stresses. Therefore, in Step 2 of the model the crater geometry predicted from Step 1 is considered as a starting surface profile. The main objective of Step 2 of the computational model (coupled with the heat transfer, fluid flow, structural mechanics, and phase change kinetics) is to predict the combinatorial effects of phase change and associated physical phenomena on the evolving surface topography.

Both computational prediction and experimental estimation of geometrical dimensions of machined region (depth and width) using computational modeling efforts and SEM image based measurements respectively assist in prediction of machining rate during laser machining of bone under a given set of machining parameters. The machining rate is considered as the volume of material removed per unit time and expressed as follows:

Machining Rate=(Cross Sectional Area of Machined Cavity)×(Laser Beam Scanning Speed)

Figure 4:
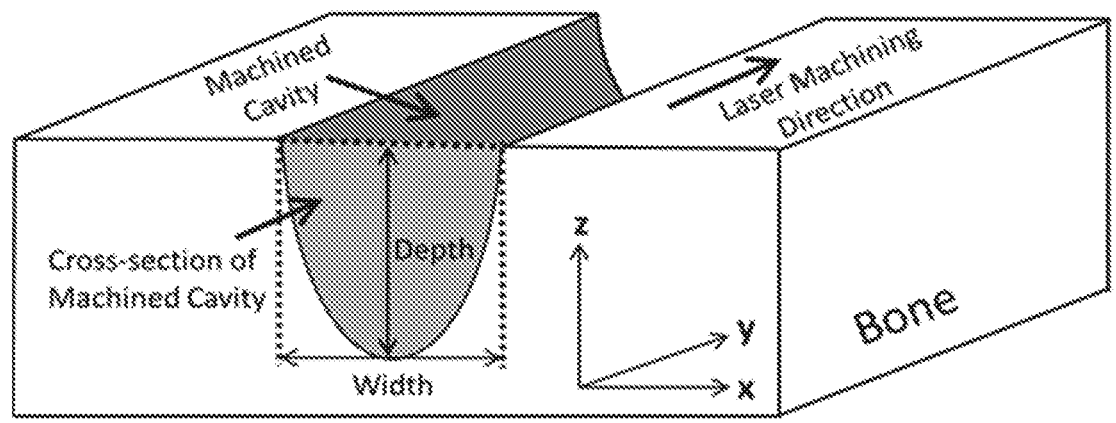
FIG. 4 shows a schematic of a cross sectional view of laser machining a portion of bone material

The schematic of computationally predicted and later experimentally confirmed cross sectional view of machined cavity appeared as a semi-elliptical geometry (FIG. 4). The cross sectional area of such portion of semi-elliptical geometry can be presented by the equation below:

$$\text{Cross Sectional Area of Machined Cavity} = \frac{\pi}{2}\left(\frac{1}{2}\text{Width}\right) \times (\text{Depth})$$

Both computational prediction and experimental estimation of width, depth, and machining rate of machined cavity are helpful for optimization of prediction/estimates and improvement of the laser based techniques for machining of bone.

Figure 5:
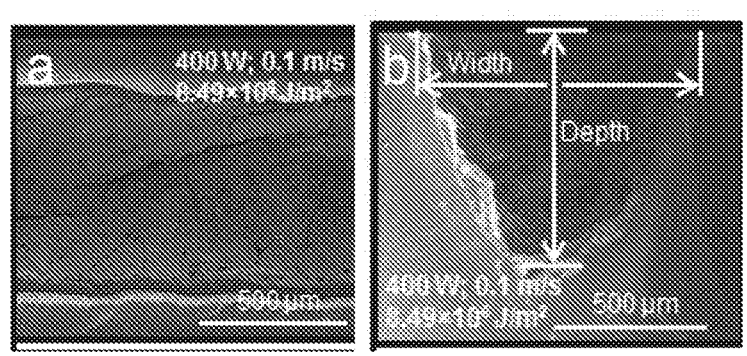
FIG. 5 shows SEM micrographs of laser ablated bone showing (a) top surface and (b) cross section showing depth and width of cut.
Figure 6:
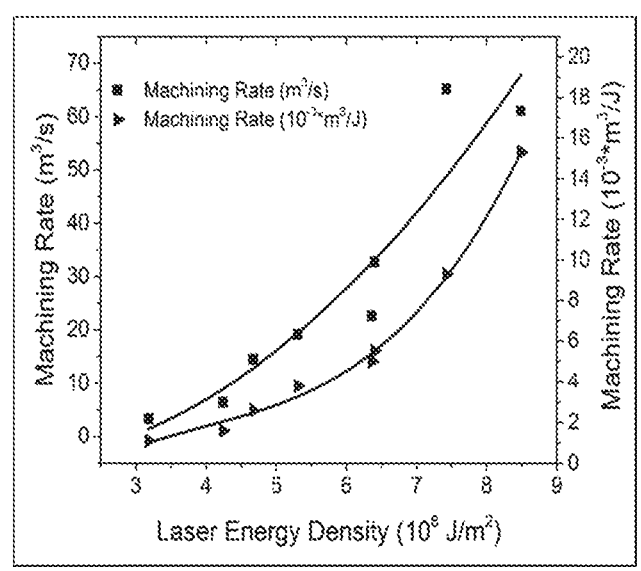
FIG. 6 shows machining rates obtained during laser cutting of bone with various energy densities.

The computational model based approach is likely to greatly help to tailor and/or fine tune the laser cutting/shaping/machining parameters to suit patient specific attributes (such as bone properties derived from other tests like MRI/CT scans) for a successful orthopaedic surgery in clinical environment. This approach is also expected to minimize the human errors and improve quality of cutting/shaping/machining by choosing the best laser parameters. Further, integration of this computational process parameter design approach with non-invasive optical sensing coupled with artificial intelligence based machine learning for precision control, safety, and localization (described in the subsequent sections) during laser cutting/shaping/machining of bone is likely to accelerate the development of a complete system for orthopaedic surgery in clinical environment. Although in certain embodiments a Er:YAG laser is preferred, preliminarily trials were carried out using Nd:YAG laser already popular for the machining of metallic and ceramic materials. Promising results have been shown with localized material removal, as shown in FIG. 5. The cutting rates were also controllable based on the laser energy density, as shown in FIG. 6.

Because biological hard tissue/bone is a non-monolithic multicomponent and multicomposition (ceramic+collagen+water+pores) material system, a given laser of specific wavelength interacts differently with each component and composition of the biological hard tissue/bone. Hence to optimize the interaction of laser with various components and compositions of the bone in terms of thermodynamic and kinetic effects, lasers that have better absorption characteristics with water are suitable for shaping biological hard tissue/bone. The lasers in the wavelength range of 1.0 to 2.93 μm tend to have better absorption with water. In light of this, Nd-YAG (1.06 μm) and Er-YAG (2.93 μm) are preferable for use during cutting/shaping/machining operations. Various combinations of input power, beam scanning speed, and operating modes (pulse and continuous) may be used as such combinations are likely to generate different thermodynamic and kinetic conditions.

In preferred embodiments, continuous wave Yb-fiber coupled Nd:YAG laser (wavelength of 1070 nm) machining of structural bone with laser power and scanning speed ranging from 300 W-700 W and 110 mm/s-250 mm/s respectively and corresponding laser fluences in the range of 3.18 J/mm$^2$-8.48 J/mm$^2$ resulted in experimentally observed machine cavities with depths, widths, and machining rates of the ranges of 136±5 μm-822±4 μm, 293±6 μm-935±20 μm, and 8±0.3 mm$^3$/s-113±0.6 mm$^3$/s respectively. A computer model incorporating various physical phenomena occurring during laser-bone interaction developed and numerically predicted the depths, widths, and machining rates in the range of 203 μm-516 μm, 412 μm-1014 μm, and 13.4 mm$^3$/s-80.3 mm$^3$/s respectively. The computer model under predicted of depth compared to experimentally observed depth at laser fluences >6 J/mm$^2$ and over predicted width compared to experimentally observed width over the entire range of laser fluences (3.18 J/mm$^2$-8.48 J/mm$^2$) which in turn resulted in under prediction of the machining rate at the laser fluences >4.75 J/mm$^2$ and >5.8 J/mm$^2$ for set of machining parameters with combinations of constant scanning speed+variable laser power and variable scanning speed+variable laser power respectively. The computationally predicted high heating ($\geq 10^4$ K/s) and cooling ($\geq 10^3$ K/s) rates supported the generation of an extensive network of microfissures confined to surfaces (with absence of penetration into the substrate) of bones machined at laser fluences ≥7.42 J/mm$^2$ of bone. The extent of network of surface microfissures gradually decreased with decrease in laser fluence. The integration of experimental and computational efforts allow for identification of an interrelationship among laser machining parameters and resultant attributes such as depth, width and machining rate of the machined cavity.

Terms: It is to be understood that this invention is not limited to particular examples, which may vary. One having ordinary skill in the art will understand that the terminology used herein is for the purpose of describing particular embodiments only, and is not intended to be limiting. In addition, before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. Additionally, when examples are given, they are intended to be exemplary only and not to be restrictive. In describing and claiming the present invention, the following terminology will be used in accordance with the definitions set out below.

It must be noted that, as used in this specification and the appended claims, the singular forms "a," "an" and "the" include plural referents unless the context clearly dictates otherwise.

The term "cutting/shaping/machining" and "shaping/cutting" refer to cutting, shaping, and/or machining and includes cutting, shaping, and machining either individually, collectively, or in combination.

The term "multiphysics computational model" as used herein refers to a set of computational processes used in correlating physical phenomena and laser processing parameters to control laser ablation/removal (cutting/shaping/machining rate) and evolution of physical attributes (cut/shaped/machined geometry) during bone cutting/shaping/machining operations.

The term "Gaussian laser beam profile" as used herein refers to a beam of electromagnetic radiation whose transverse electric field and intensity (irradiance) distributions are well approximated by Gaussian functions.

The term "top hat laser beam profile" as used herein refers to a beam of electromagnetic radiation whose transverse electric field and intensity (irradiance) distributions are constant and uniform over the cross section of the beam.

The term "dumbbell laser beam profile" as used herein refers to a beam of electromagnetic radiation whose power intensity distribution is relatively more intense at the outer regions than in the central region.

The term "bone" as used herein refers to rigid organs that constitute part of the endoskeleton of vertebrates. They support and protect the various organs of the body, produce red and white blood cells and store minerals. Bone tissue is a type of dense connective tissue. Bones come in a variety of shapes and have a complex internal and external structure, are lightweight yet strong and hard, and serve multiple functions. Bones may also be considered for this invention to be synthetic bones or bone replacement material, including metals and ceramics.

The term "laser energy density" as used herein refers to a parameter of LAM calculated as follows: Laser energy density (J/m$^2$)=(Laser power (J/s)/laser irradiation area (m$^2$))×(laser beam diameter (m)/scanning speed (m/s)).

The term "bone tissue machining rate" as used herein refers to a machining rate (m$^5$/Js)=Volume of material removed (m$^3$)/residence time (s)/laser energy density (J/m$^2$)

The term "Real time clock controller" (RTC-controller) provide synchronous, interference-resistant control of scan systems and lasers in real time. A signal processor and dynamic link libraries ("DLL") can simplify programming. Alternatively, software from various third-party vendors is also available for handling standard applications. For example, instructions can be loaded in the RTC, processed, and output as 16-bit control signals every 10 µs to the scan system. The RTC-controller can automatically performs vital steps such as micro-vectorization and image field correction. Laser control is synchronized with the scanner movements.

The term "z" as used herein refers to the Z-coordinate in a three dimensional space (m)—(Direction of laser beam motion within the surface plane of substrate).

The term "x" as used herein refers to X-coordinate in a three dimensional space (m)—(Direction normal to the laser beam motion Z, within the surface plane of substrate).

The term "y" as used herein refers to Y-coordinate in a three dimensional space (m)—(Direction normal to both the laser beam motion and the surface plane of substrate, Z and X and along the beam axis).

The term "$\rho$" as used herein refers to Density (kg/m³).

The term "$C_p$" as used herein refers to Specific heat at constant pressure (J/kg·K).

The term "T" as used herein refers to Temperature (K, Kelvin).

The term "t" as used herein refers to Time (s, seconds).

The term "K" as used herein refers to Thermal conductivity (W/m·K).

The term "$\varphi$" as used herein refers to Laser on/off function.

The term "$P_X$" as used herein refers to the three dimensional laser power intensity distribution (W/m²).

The term "$P_g$" as used herein refers to the three dimensional Gaussian laser power intensity distribution (W/m²).

The term "$P_{th}$" as used herein refers to the three dimensional top hat laser power intensity distribution (W/m²).

The term "$P_{db}$" as used herein refers to the three dimensional dumbbell laser power intensity distribution (W/m²).

The term "$P_o$" as used herein refers to the average input laser power intensity (W/m²).

The term "$r_o$" as used herein refers to the radius of beam at which laser power transverse intensity decreases to $$\frac{1}{e^2}$$

The term "$M_{bone}$" as used herein refers to the average thermophysical and/or themomechanical properties of the bone.

The term "$M_{mineral}$" as used herein refers to the thermophysical and/or themomechanical properties of the mineral component of bone.

The term "$M_{collagen}$" as used herein refers to the thermophysical and/or themomechanical properties of the collagen component of bone.

The term "$M_{water}$" as used herein refers to the thermophysical and/or themomechanical properties of the water component of bone.

The term "$M_{porosity}$" as used herein refers to the thermophysical and/or themomechanical properties of the porosity component of bone.

The term "$X_{mineral}$" as used herein refers to the volume fraction of the mineral component of bone.

The term "$X_{collagen}$" as used herein refers to the volume fraction of the collagen component of bone.

The term "$X_{water}$" as used herein refers to the volume fraction of the water component of bone.

The term "$X_{porosity}$" as used herein refers to the volume fraction of the porosity component of bone.

The term "h" as used herein refers to Heat transfer coefficient (W/m²·K).

The term "$T_i$" as used herein refers to Initial temperature (K).

The term "$\varepsilon$" as used herein refers to Emissivity.

The term "$\sigma$" as used herein refers to Stefan-Boltzmann constant (W/m²·K⁴).

The term "$t_r$" as used herein refers to Laser beam residence time (s)=Diameter of laser beam/Scanning speed.

The term "P" as used herein refers to Laser beam power (W, Watts).

The term "D" as used herein refers to Diameter of laser beam (m, Meters).

The term "v" as used herein refers to Laser Beam Scanning Speed (m/s).

The term "$T_0$" as used herein refers to ambient temperature.

The term "$\phi$" as used herein refers to the standard deviation of laser beam intensity.

The term "$L_v$" as used herein refers to latent heat of vaporization.

The term "$M_v$" as used herein refers to mass of vapor molecule.

The term "$T_s$" as used herein refers to instantaneous surface temperature.

The term "$T_v$" as used herein refers to instantaneous vaporization temperature.

Additional defined terms used herein have the meanings provided.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Thermal Interactions in Continuous and Long Duration Pulsed Lasers

During laser irradiation of bones and hard tissues, temperature rise as a result of heat input leads to occurrence of various thermal interactions. These interactions are very significant from the machining point of view and can take place in continuous as well as pulsed laser operation. Depending on the temperature and duration of exposure, the effects resulting of the thermal interactions include coagulation, carbonization, melting, and vaporization. As these thermal effects may lead to significant material damage, the processing in this regime requires a careful process control. Coagulation (clotting of the blood cells) occurs at temperatures of 60° C. whereas carbonization commences at 100° C. With further increase in temperature, occurrence of melting is followed by vaporization leading to thermo-mechanical ablation. Thermal effects are usually observed in case of continuous and long duration pulsed type of $CO_2$, Nd:YAG, Er:YAG, Ho:YAG, argon ion, and diode lasers.

Thermal ablation effects have been heavily explored in laser cutting/shaping/machining of the bones. In one such study, comparison was done between the material removal characteristics of parietal bone of a rat during drilling operation with a burr and Er:YAG laser (wavelength of 2.94 mm, an output range of 30-350 mJ/pulse, a maximum pulse repetition rate of 10 Hz, and pulse duration of 200 microseconds), and a $CO_2$ laser (wavelength of 10.6 mm and output range of 0.5-5 W). Energy output of 100 mJ/pulse was found to be clinically appropriate. Laser power employed was 1 W and bur drill was angled at 30°. Er:YAG laser resulted in grove formation, and two distinct layers were observed on the machined surface. The drilled boundaries were precise and the average affected depth was 22 μm. $CO_2$ laser did not result in groove formation and damaged region was much larger. The laser affected region was divided in three zones: a completely carbonized layer on the irradiated surface, a mildly carbonized intermediate layer, and a darkly stained layer at deeper sites of irradiation. Bur drill as expected, resulted in grove formation with presence of smear like region.

TEM analyses indicated in case of Er:YAG laser irradiated bone that well oriented crystals were present in the unaffected region whereas less affected region revealed partly disorganized crystals. Surface had totally random orientation. All the regions had crystalline diffraction pattern. In case of $CO_2$ laser, partially carbonized region indicated round and large crystals. Fully carbonized layer displayed complete fusion of the original apatites. Bur drilling had an unaffected region similar to in case of Er:YAG laser, but smeared layer had a mixture of amorphous phase and needle like crystals. This suggested that Er:YAG and bur drilling induced minimum damage in the regions underneath. EDS analysis suggested changes in Ca/P ratio in case of the Er:YAG laser and reason was thought to be formation of meta stable phases.

Even though bur and Er:YAG generated least damage in the bone, the post operation recovery was better in case of Er:YAG making it most beneficial method. The mechanism of ablation takes into account the composite nature of the bone. The differential thermal properties of bone constituents lead to thermo-mechanical effects. The steps in ablation mechanism are as follows: (1) The absorption of laser energy by the bone results in rise in temperature. Water content within the bone starts to boil building a vapor pressure. (2) The built up pressure leads to a micro explosion. The micro-explosions eventually produce mechanical tissue ablation. (3) A two layered structural zones are generated where in subsurface layer which accumulated energy undergoes micro explosions whereas surface with direct exposure to the intense laser energy instantly undergoes micro cracking.

Another study has compared ablation characteristics of Er:YAG, continuous wave $CO_2$, and a pulsed $CO_2$ laser. Er:YAG again was proved to be the best laser by providing least damage to the exterior of the bone as well as the cartilage and machining was achieved at much faster rates at lower energy densities. This was attributed to 10 times higher absorption coefficient of bone at 2.94 μm wavelength of Er:YAG laser than that of $CO_2$ laser of 10.6 μm. In addition, pulsed lasers were found to be helpful because they allowed a cool down time.

Apart from Er:YAG and $CO_2$ lasers, other types of lasers causing thermal effects also have been tried for the bone ablation process. Nd:YAG ($\lambda$=1:06 mm, $\tau_L$=100 μs-cw) and Ho:YAG ($\lambda$=2.12 nm, $\tau_L$=150-800 μs) have been used in majority during these studies because of the main advantage that these lasers can be conveniently transmitted via a glass fiber. From practical point of view, this characteristic becomes very important because in an actual surgery setup, maneuverability of the surgical tools plays a key role in order to carry out the operations optimally. Thus, with the usage of transmittable lasers, it is possible to keep the laser system away from the patient and surgeons and transmit the beam via fiber to a hand held laser head thereby providing a lot of convenience. Nonetheless, these lasers induce undesired damage within the bones. The wavelengths of these lasers are strongly scattered by the water as well as the mineral with scattering of the order of 350-400 $cm^{-1}$. Uneven distribution of energy leads to heavy damage to the bone tissues. Apart from these commercially available medical lasers, other types of lasers such as $Nd:YVO_4$ and free electron laser (FEL) have been tried successfully for bone material removal. $Nd:YVO_4$ laser resulted in heavy carbonization (charring) during ablation. A tunable FEL was used for investigating effect of various wavelengths (2.79, 2.9, 6.1, and 6.45 μm) on the bone ablation. The wavelength of 6.1μ was the most efficient in terms of ablation and had least thermal damage on the bone tissues. The reason was again related to optimum absorption of this wavelength by water as well as bone mineral.

Example 2

Apparatus for Laser-Assisted Machining ("LAM") of Bone

The present invention relates to a system involving a process and apparatus for laser-assisted cutting/shaping/machining ("LAM") of bone. The LAM provides high precision dimensional machining with minimal or no surrounding tissue damage/trauma. The non-contact, highly-focused laser beam integrated with a robotic-computer controller, offers highly-precision dimensional matching for any complicated structural bones. The afore mentioned technique follows simple procedure and is expected to facilitate rapid recovery without traumatic vibrational related injury, negligible heat-mark and minimal invasive tissue damage that are typically associated with conventional orthopedic techniques and also requiring no blood transfusions.

In one embodiment, the present invention comprises an apparatus for laser-assisted bone machining, comprising: a) a laser; b) a personal computer; c) a real time clock/controller (RTC); d) a beam expander; e) a dynamic focusing unit, such as a varioSCAN®; f) a power supply; g) a scan head; and h) an objective.

The dynamic focusing unit (e.g. a varioSCAN® by SCANLAB™) in some embodiments of the invention enables precise, high-performance positioning of the laser focus along the optical axis. In XY scan systems, a dynamic focusing unit can replace costly flat field objectives. Therefore, the dynamic focusing unit is an ideal solution in applications for which standard flat field objectives are unavailable. The dynamic focusing unit can also extend XY scan systems into 3D beam deflection systems. The laser focus is guided along the contour of the workpiece being processed, thus enabling processing in three dimensions. The dynamic focusing unit additionally allows continuously adjusting the image field size, working distance and spot size. Some models of the dynamic focusing unit offer much lower tracking error, resulting in a larger focus-shift range and better spot quality.

The RTC in some embodiments of the invention serves two purposes: 1) keep accurate time/date information; and 2) provide wake up alarms (both during runtime and while sleeping). Since the RTC is externally powered and clocked independently of the processor, it can remain running even when the rest of the system is turned off. An RTC controller card is a mode of communication between a PC and a laser beam scanner, and provides information instantly or with negligible latency.

Figure 7A:
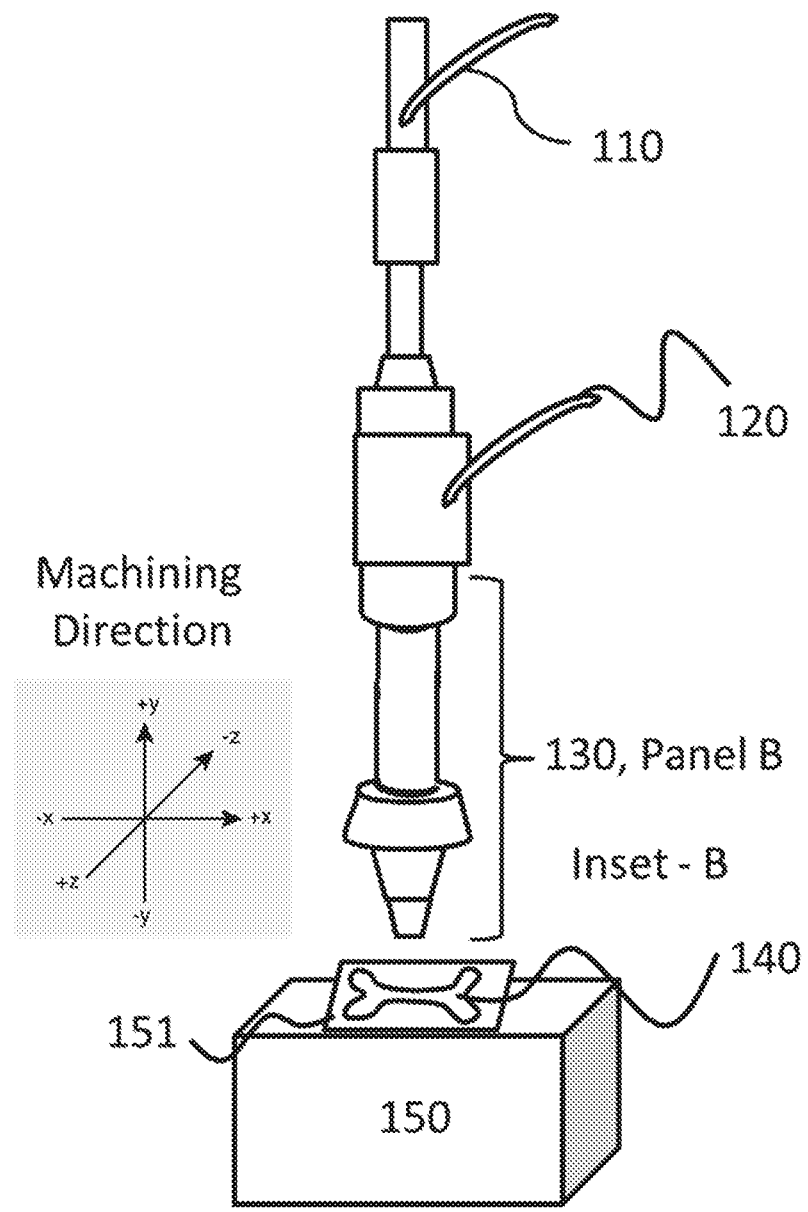
FIG. 7A shows an illustration of an example of a laser system for laser-assisted bone cutting/shaping/machining.
Figure 7B:
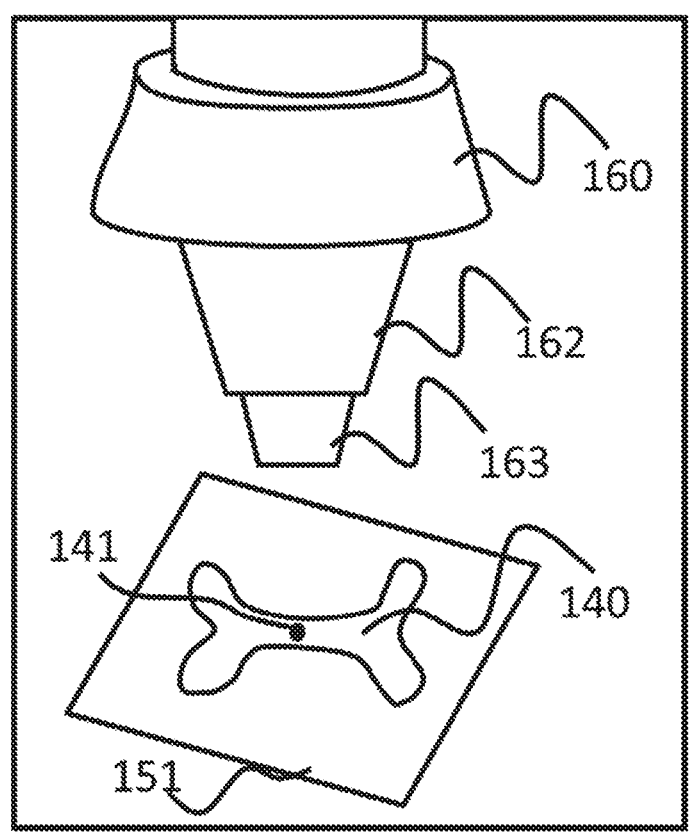
FIG. 7B shows an enlarged illustration of a bone sample undergoing cutting/shaping/machining.

Turning now to FIGS. 7A and 7B, which shows a laser system for laser-assisted machining (LAM) of bone includes a laser device. FIG. 7A according to the present disclosure includes a system having a laser attached electrically and through fiber optics (110). A protective gas line (120) is in fluid communication with the LAM of bone system. A bone sample (140) is shown on a fixture (151) that is on top of a guiding device (150). The laser beam spot (141) is focused on the bone sample (140) using a beam focusing head (130). FIG. 7B shows the laser beam and gas nozzle outlet (160); scale dial for adjusting the protective/cover gas flow (162); and the collar of focusing head (163). The synchronized control of scan systems, lasers and guiding systems is completed using real time controller boards, or computers integrated with each component of the system. In FIGS. 7A and 7B, the focusing head motion is CNC controlled and integrated with the robotic motion system allowing the machining to be completed in a multi-dimensional space.

Figure 7C:
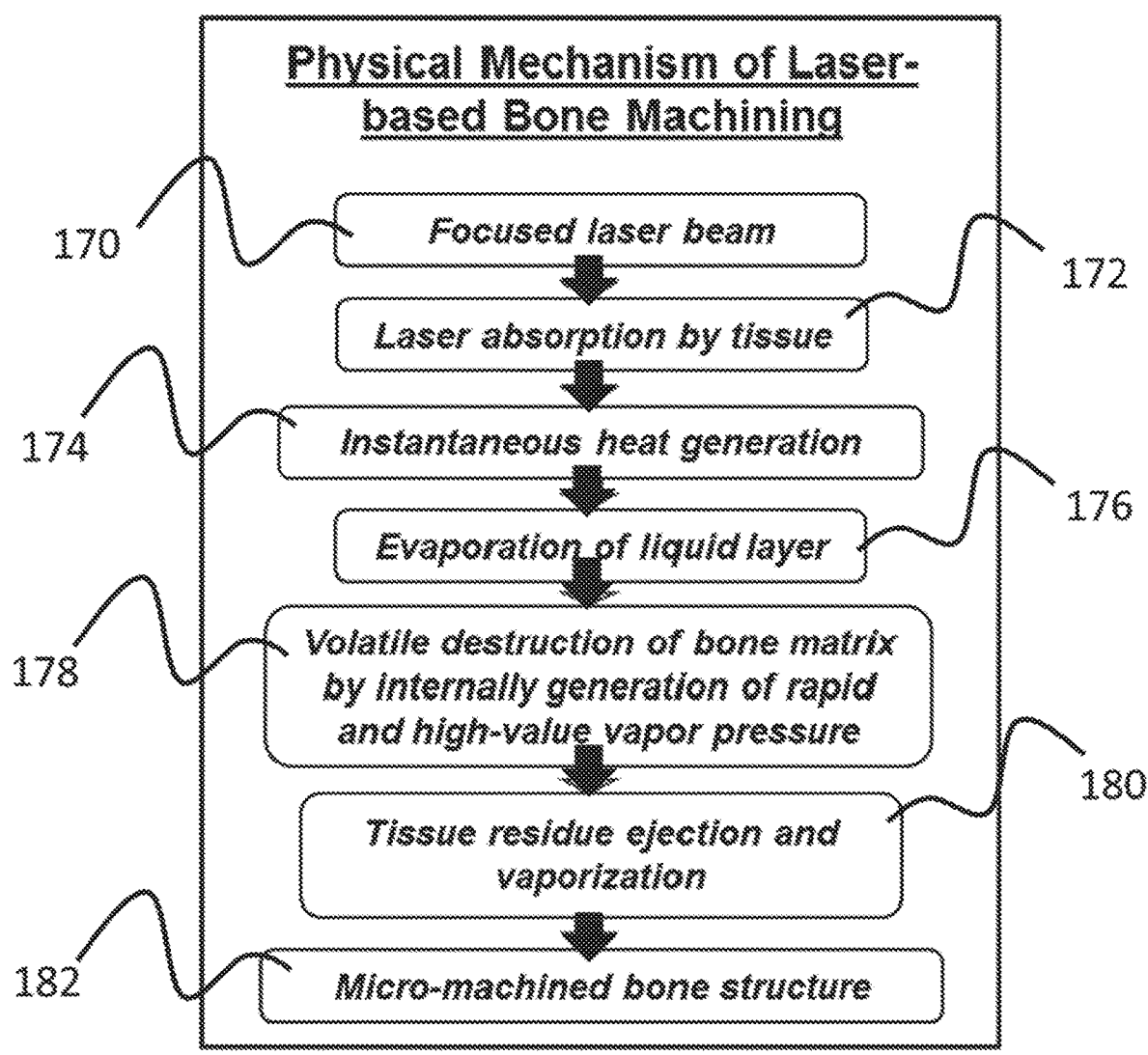
FIG. 7C shows exemplary sequential physical mechanisms utilized in embodiments of laser based bone cutting/shaping/machining.

Although not wanting to be bound by theory, FIG. 7C describes the sequential physical mechanisms of laser base bone machining. For example, by providing a narrowly focused laser beam (170) on a bone sample will allow laser absorption by the bone tissue (172). The absorption of energy causes the instantaneous heat generation (174) within the bone tissue and the evaporation of a liquid layer and organic/inorganic bone components (176). A volatile destruction of bone matrix occurs due to an internal generation of rapid and high-value vapor pressure (178). The bone tissue residue ejection on vaporization occurs (180), wherein a micro-machined bone structure remains (182). This embodiment essentially comprises: a) observing a region of bone to be cut/shaped/machined; b) calculating the temperature-bone component (mineral, collagen, water, and porosity) dependent material properties of the region of bone; c) determining parameters for laser-assisted machining based on the temperature-dependent material properties of the region of bone; and d) performing laser-assisted bone machining using the determined parameters.

Figure 8B:
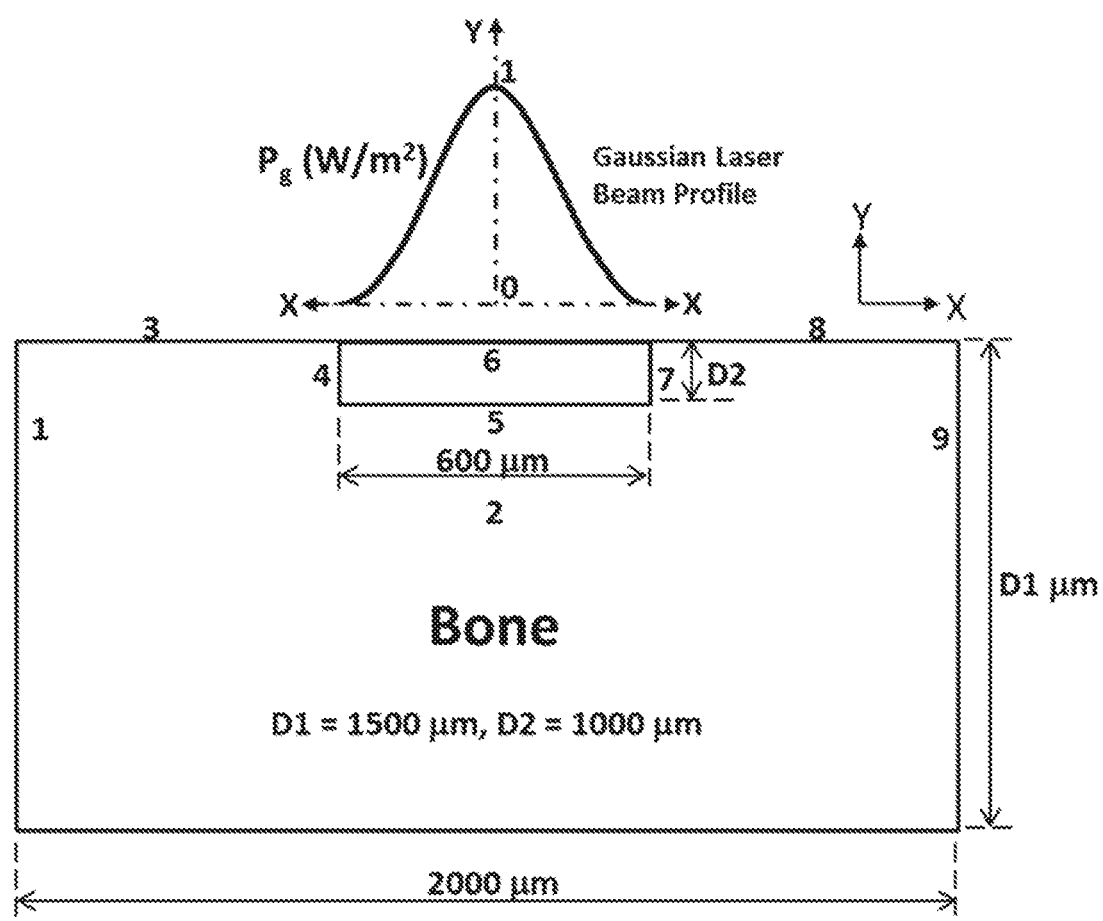
FIG. 8B shows the boundary conditions of a computational model used in accordance with exemplary embodiments of the present disclosure to represent temperature-dependent material properties of a region of bone.

Although not wanting to be bound by theory, bone comprises ceramic/mineral components such as calcium phosphate and hydroxyapatite (HA); organic components such as collagen; water and porosity. In order to provide governance to the process, a computational model of bone was developed. More specifically, FIG. 8A shows the computational model used to represent the temperature-dependent material properties for bone. The governing equations for the computational model are shown in Table 1 of FIG. 8A, with references directed to FIG. 8B. As the beam is axisymmetric in terms of laser power intensity distribution in the plane (x-z) orthogonal to the axis (y) of the laser beam, the mathematical formulation is considered in 2D (x-y) plane.

Turning now to FIG. 8A and FIG. 8B. The boundary conditions for the whole geometry can be modeled using the governing equation:

$$\rho c_p \left[ \frac{\partial T}{\partial t} \right] = k \left[ \left( \frac{\partial^2 T}{\partial x^2} \right) + \left( \frac{\partial^2 T}{\partial y^2} \right) \right].$$

The boundary conditions for heat flux, natural convection cooling and radiation is represented in FIG. 8B, for area 6, has the model equation of:

$$-k \frac{\partial T}{\partial y} = \varphi P_g - h[T - T_i] - \varepsilon\sigma[T^4 - T_i^4]$$

where, $\varphi=1$ for $0 \leq t \leq t_r$, and $\varphi=0$ for $t \geq t_r$.

Additionally, the boundary conditions for the average laser power density in Gaussian distribution is represented in FIG. 8B, for area 6, has a the model equation of:

$$P_g = \frac{P_0}{\pi r_0^2} \exp\left[-\left[\frac{x^2+y^2}{r_0^2}\right]^2\right]$$

The boundary conditions for natural convection cooling and radiation in FIG. 8B, areas 1 and 9, has a model equation of:

$$-k \frac{\partial T}{\partial x} = h[T - T_i] - \varepsilon\sigma[T^4 - T_i^4]$$

The boundary conditions for natural convection cooling and radiation in FIG. 8B, areas 3 and 8, has a model equation of:

$$-k \frac{\partial T}{\partial y} = h[T - T_i] - \varepsilon\sigma[T^4 - T_i^4]$$

The boundary conditions for insulation in FIG. 8B, area 2, has a model equation of:

$$\frac{\partial T}{\partial y} = 0$$

Example 3

Machining Parameters

In specific embodiments, the process may utilizes one or more techniques to determine one or more physical characteristics of the bone to be machined, such as X-ray Computed Tomography (X-ray CT), Single Photon Emission CT (SPECT), Magnetic Resonance Imaging (MRI), Micro-Position Emission Tomography (microPET), Fluorescence Molecular Tomography (FMT), Mouse-Dual Energy X-ray Absorptiometry (DEXA) and to determine the density (i.e. porosity) of the bone which in turn provides the estimate for total volume fraction of the components of bone (calcium phosphate-hydroxyapatite, collagen, water, and porosity) along with the estimates of elemental compositions and volume fractions of each of these bone components (calcium phosphate-hydroxyapatite, collagen, water, and porosity).

Although not wanting to be bound by theory, knowing the thermo-physical properties such as thermal conductivity, specific heat, and density of each bone component from the literature, the thermo-physical properties of a given bone matrix (composite) may be computed. These thermo-physical properties, along with the dimensions of bone and boundary conditions are incorporated into the multiphysics based computational model of the present invention to predict the temperature-time history for cutting/shaping/machining a given bone. Although not wanting to be bound by theory, knowing this history, various laser parameters such as laser power and scanning speed may predicted to machine a given bone for required dimensions with the desired machining rate.

Bone's cut/shaped/machined depth (d in μm) is a function of temperature (T in K):

$$d=f(T)$$

Temperature is a function of laser energy density (LED in $J/m^2$):

$$T=f(LED)$$

Laser energy density is the function of laser power (P in W), beam focal spot diameter (D in m), and laser beam scanning speed (v in m/s):

$$LED=f(P,diam,v)$$

The laser-assisted bone machining apparatus and process of the present invention exhibit several advantages over conventional technology. The present invention provides a chemically clean light source for cutting/shaping/machining. A coherent and monochromatic beam is delivered to the region to be cut/shaped/machined, which provides narrow beams, high power density, and little or no heat affected zone ("HAZ") without physical contact and hence without mechanical loading and frictional forces. A flexible fiber optics beam allows for remote processing and is amenable to processing complex shapes quickly and easily. Finally, laser assisted machining (LAM) of bone integrated with a robotic-computer controller provides a highly precise method for cutting/shaping/machining complicated structural bones. The technique is also expected to facilitate rapid recovery with minimal traumatic injury, negligible heat-mark, and minimal invasive tissue damage that are typically associated with conventional orthopedic techniques.

Figure 9B:
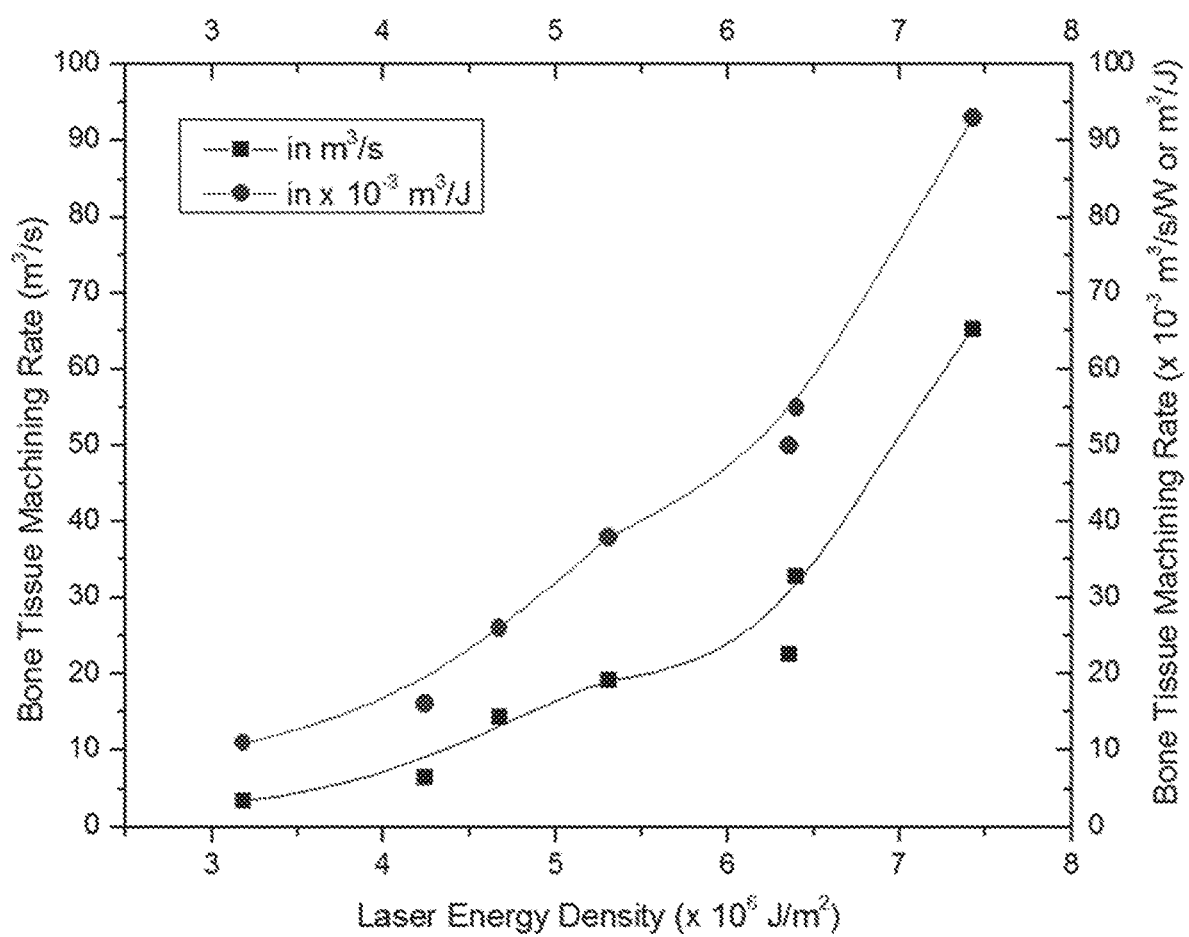
FIG. 9B shows a graphic representation of bone tissue cutting/shaping/machining rate as a function of laser energy density in accordance with exemplary embodiments of the present disclosure.
Figure 9C:
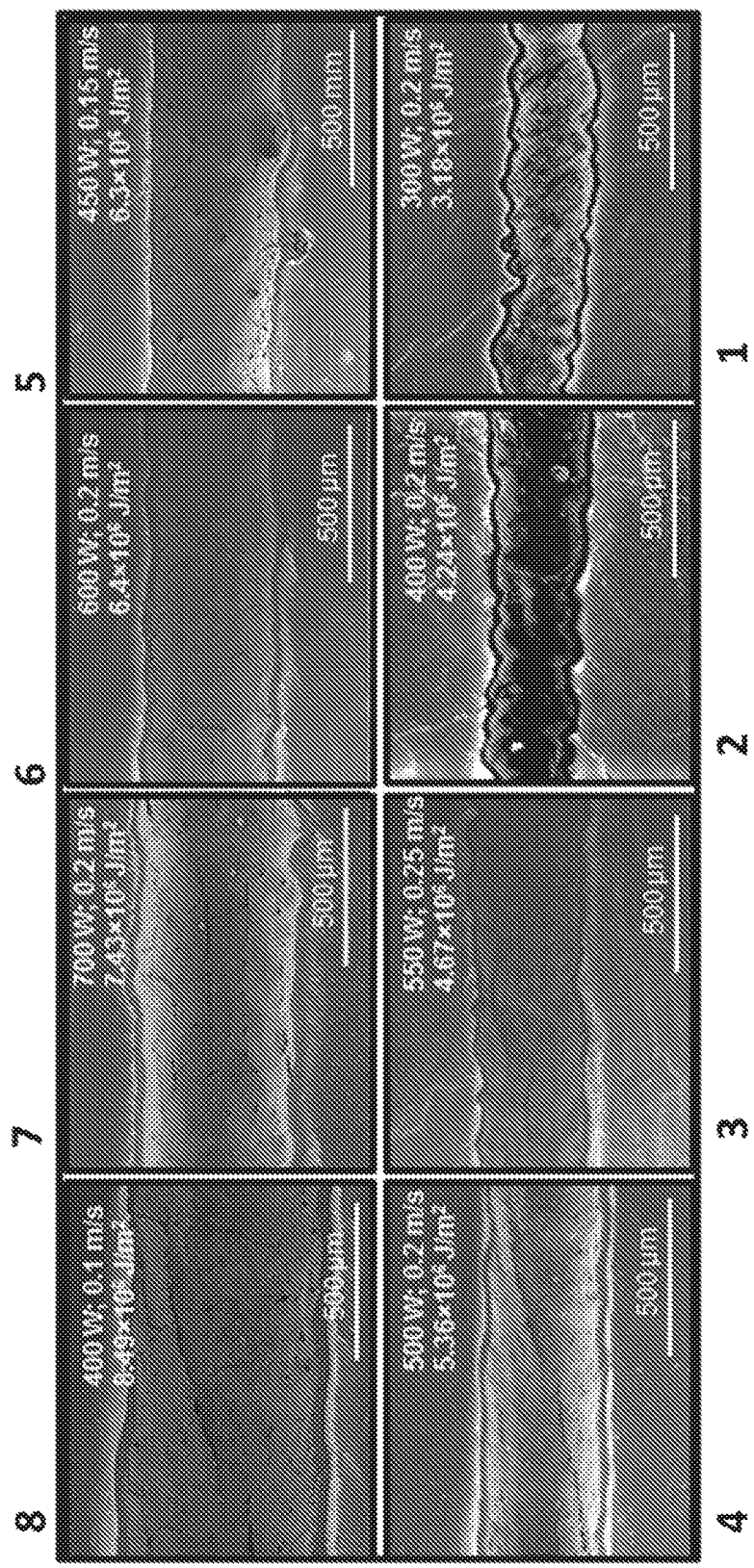
FIG. 9C shows scanning electron microscopy (SEM) surface views of the width of a laser based bone cut/shaped/machined sample according to exemplary embodiments of the present disclosure.
Figure 9D:
FIG. 9D shows SEM images of cross sectional views (i.e. width and depth) of laser-assisted bone cut/shaped/machined samples in accordance with exemplary embodiments of the present disclosure.

Turning now to FIG. 9A. The laser-assisted machining of bone was performed using eight different sets of parameters, wherein machining attributes and rates were measured. FIG. 9B shows bone tissue machining rate as a function of laser energy density for the experiments shown in FIG. 9A. FIG. 9C is an illustration showing the width of each of the eight parameters of FIG. 9A. In addition, FIG. 9D is an illustration showing the depth of each of the eight parameters of FIG. 9A. For example, the row of parameters listed in Experiment 1 of FIG. 9A indicate the following parameters: the laser power (W)=300 W; Scanning speed=0.2 m/s; Residence time=3.0 ms; Laser energy Density=$3.18 \times 10^6$ $J/m^2$; giving a machining rate=3.3 $m^3/s$ or a machining rate representing a volume of material removed ($m^3$)/residence time/laser energy density ($J/m^2$). The experimental width of bone cut using these parameters is shown in FIG. 9C (Panel 1). Similarly, the experimental depth of bone cut using these parameters is shown in FIG. 9D (Panel 1). The laser machining attributes of bone either measured computationally, or experimentally are compared in FIG. 9C.

Figure 10:
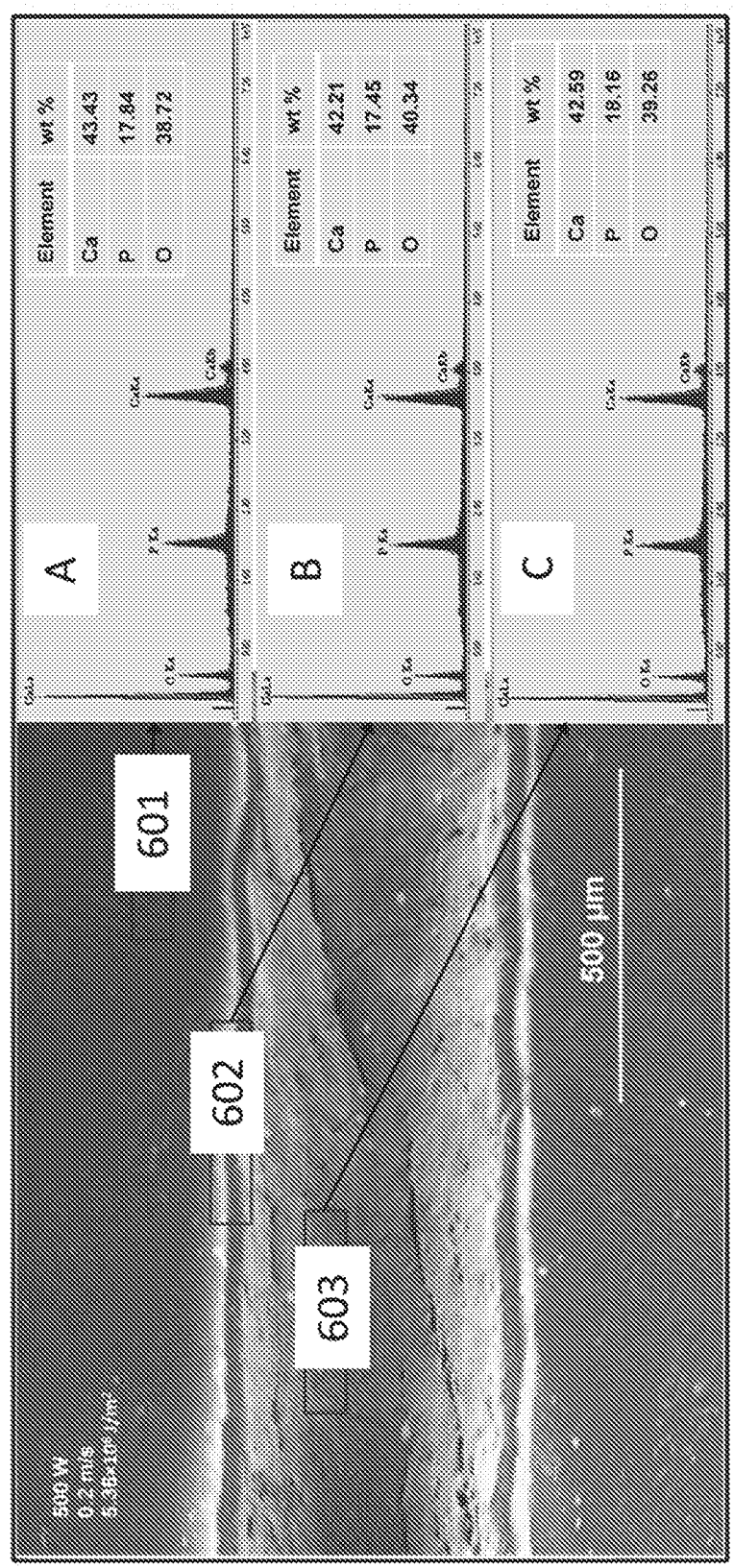
FIG. 10 shows an SEM view of laser cut/shaped/machined bone sample at $5.36 \times 10^6$ J/m$^2$ laser energy density, showing several cut/shaped/machined regions and the corresponding elemental composition within these regions in accordance with exemplary embodiments of the present disclosure.

Turning now to FIG. 10, showing an illustration laser machined bone sample at $5.36 \times 106$ J/m2 laser energy density. FIG. 10 shows several machined regions (601, 602, and 603) and the corresponding elemental composition within these regions (601—Panel A, 602—Panel B, and 603—Panel C). More specifically, Region 601 and Panel A correspond to the base bone material. Region 602 and Panel B correspond to the heat affected zone surrounding machined region. Region 603 and Panel C correspond to the machined bone area.

Figure 11:
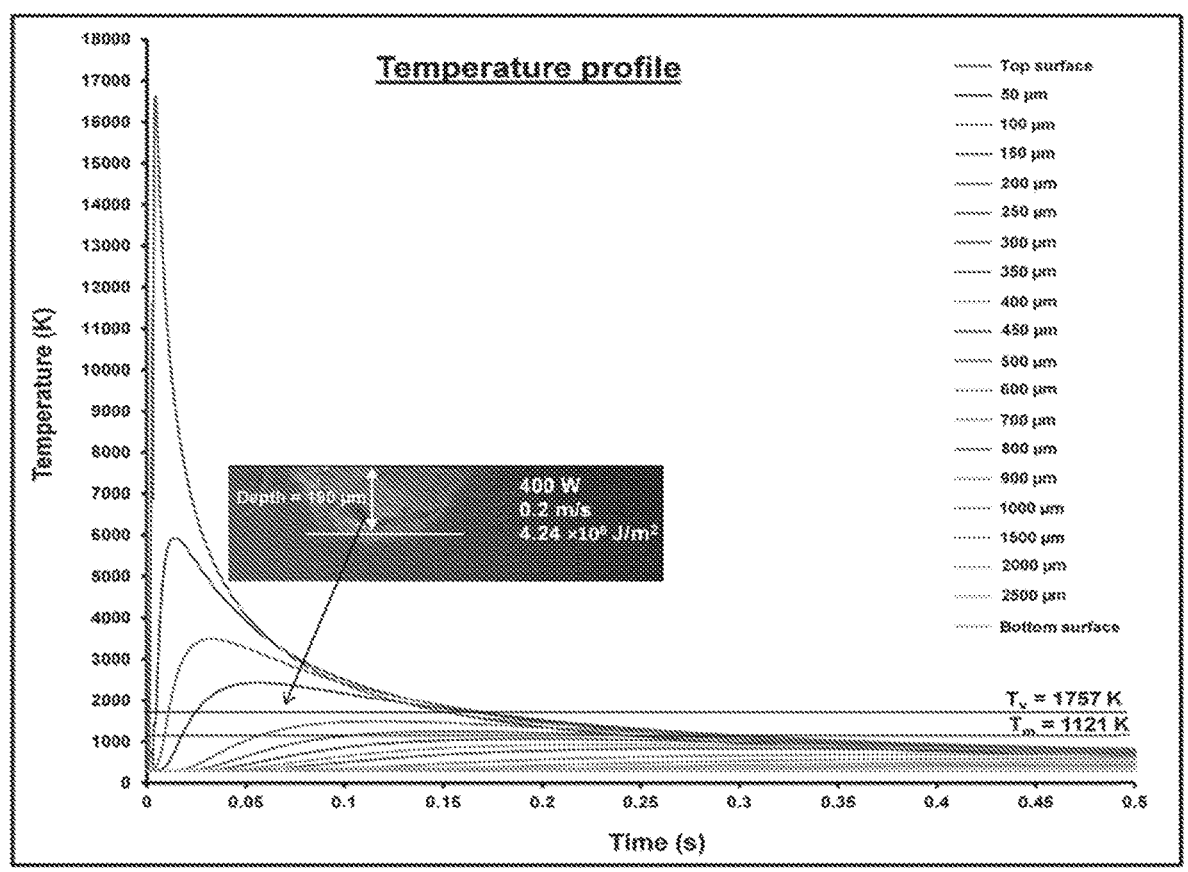
FIG. 11 shows temperature profiles at different depths for laser cut/shaped/machined bone sample at $4.24 \times 10^6$ J/m$^2$, according to one process of the present invention.

In summary, when the highly focused laser beam was applied on the bone surface in shorter time scale (2-4 ms) due to laser absorption by bone tissue, the rapid generated heat intensity ($4.2-9.9 \times 10^7$ $W/m^2$) was penetrated into the bone tissue that in turn created vapor pressure and plasma. The protruded plasma has further destructed the bone matrix deeply, which caused the ejection of residue of machined bone tissue. Depending on the applied laser energy density (combination of laser power, laser beam traverse speed and beam size on the bone surface) and corresponding cooling rate, various levels of volume of bone removal and corresponding bone machining rate can be achieved with minimal or not heat affected zone surrounding the machined region. Furthermore, such a combination of machining parameters raise the temperature within the laser beam-bone interaction region at the level (FIG. 11) that machines the bone without damaging the tissues in the regions surrounding the machined area. Such carefully selected laser machining parameters also allow preserving the composition of bone tissue within the machined regions same as the surrounding region and the base bone material.

Example 4

LAM of Bone with Computer Numeric Controlled Robotics

Figure 12:
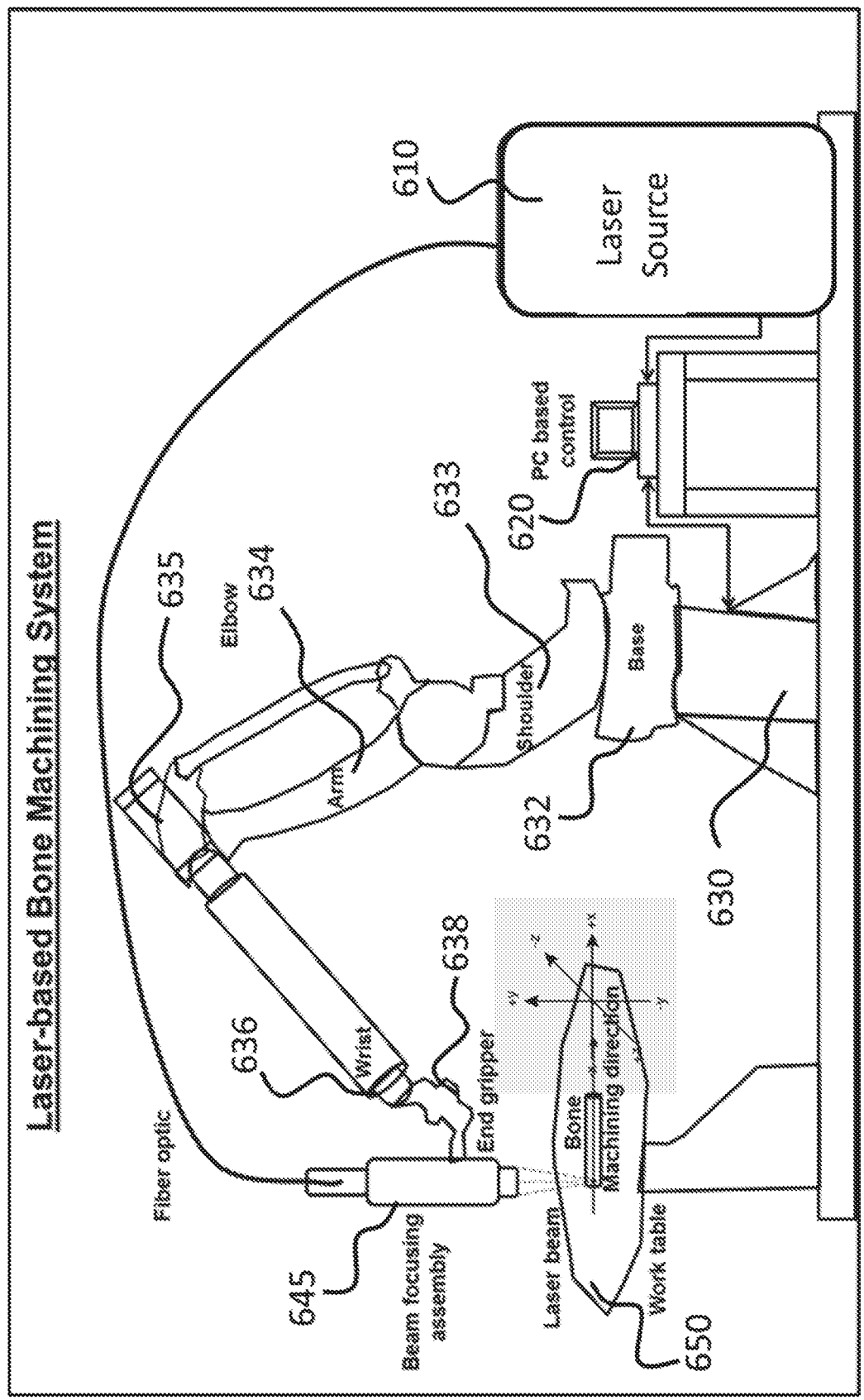
FIG. 12 shows an automated computer numeric controlled ("CNC") bone cutting/shaping/machining system, in accordance with exemplary embodiments of the present disclosure.

The uniqueness of the current invention with regard to the elements is shown in FIG. 12, which represents an automated bone milling system. More specifically, both hard tissues and bones are composed of multiple components such as organic (collagen), inorganic (calcium phosphate), water and porosity that in turn exist in various volume fractions and physical formats. These components have different thermo-physical properties. Hence, in order to cut/shape/machine these tissues in complex configurations with high accuracy and speed without damaging the surrounding tissues, the laser parameters (power, scan speed, beam focus) and motion system (robot) parameters (speed and position) required to be synchronized and controlled accurately/precisely. This is possible through the control and synchronization of the general elements of the milling system depicted in FIG. 12.

Turning now to FIG. 12, a laser source (610) is in fiber optical connection with the beam focusing assembly (645). The laser source is also in electrical communication with a controller device, in this case it is a computer (620). The computer is also in electrical communication with the robotic arm. The robot sits on a stand (630), having a base (632) that is in mechanical and electrical communication with the shoulder (633), the arm (634), the elbow (635), the wrist (636) and the end gripper (638). The end gripper of the robotic arm (638) is attached to the beam focusing assembly (645) and can be controlled using the computer (620). A bone sample (641) located on the work table (650) can be cut/shaped/machined using the automated robot arm integrated with the laser source.

The technique is a non-contact simple procedure this is also a flexible method. The laser beam can be delivered via fiber optic to the bone that is being machined. Such a laser beam delivery can be achieved with either a manually operated hand held devices or by a computer numeric controlled ("CNC") robotic system for full automations (FIG. 12). In both cases, the vision system can be integrated with the beam delivery system for beam guidance during cutting/shaping/machining simple as well as complex profiles. Due to the fiber optic delivery based approach, the laser can be situated and operated remotely. Both, laser operation (for power adjustment) and beam motion system, if it is fully robot based, can be computer numeric controlled for height precision. Furthermore, the envelope for operating parameters and the types of tissue materials (hard and soft) that can be handled (machined) can be extended employing many types of lasers (infrared and ultraviolet wavelength range) in both manual, semi-automated and fully automated cutting/shaping/machining operations.

The present invention provides a process for laser-assisted bone cutting/shaping/machining. In one embodiment, the process comprises the steps of: a) providing a focused laser beam; b) laser absorption by tissue; c) instantaneous heat generation; d) evaporation of a liquid layer and organic/inorganic components of the bone; e) volatile destruction of bone matrix by internal generation of rapid and high-value vapor pressure; and f) tissue residue ejection and vaporization, resulting in micro-machined bone structure.

Example 5

LAM of Bone Using Dumbbell Laser Profile

Figure 13:
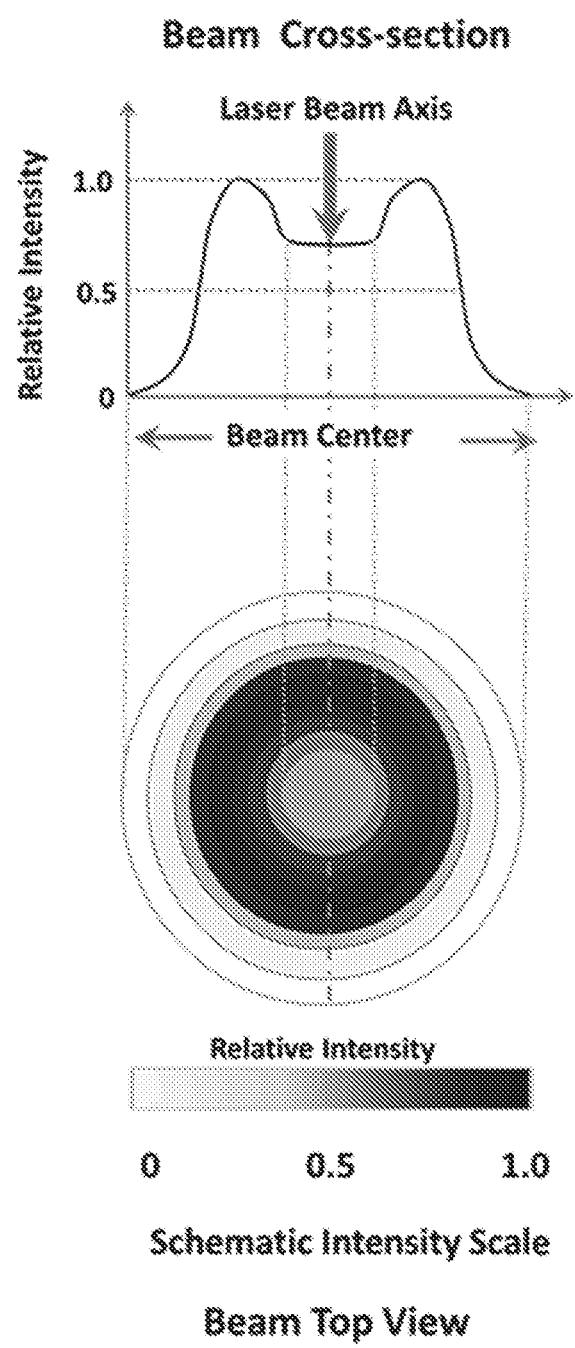
FIG. 13 shows a schematic of dumbbell laser beam profile in cross sections parallel and orthogonal to the beam axis along with laser power intensity distributions within these sections.

The dumbbell laser profile presents a laser power intensity distribution relatively more intense at the outer regions than in the central region. More precisely, such laser beam comprises a central region and two outer regions. Each of the outer regions comprises an outer edge. Such composite beam possesses a power intensity distribution that is in average constant in the central region followed by increased power intensity at the outer region which eventually decreases at the outer edges such that the peak outer to average central power intensity ratio of the dumbbell laser beam profile is greater than or equal to 1.2. The schematic of such dumbbell laser beam profile is presented in FIG. 13.

Employment of such dumbbell laser beam profile during bone machining compensates for the excessive heat transfer in the workpiece (bone) region surrounding the beam and produces uniform temperature rise within both central region and the edge region of the laser beam workpiece (bone) interaction zone. Thus, the constant distribution in the central region provides substantially uniform energy deposition and material processing in the central region. The increased power distribution at the outer regions compensates for the increased energy or heat flux in this region. The substantially step function decrease in power distribution at the end regions provides for controlled material processing in a region approximately equal to the width of the power intensity distribution. This provides improved cutting/shaping/machining where the laser beam is applied to the workpiece (bone) along contiguous parallel paths by minimizing or eliminating the need for overlap between subsequent parallel laser tracks.

Such uniform heat transfer throughout the laser beam material (bone) interaction zone generates several advantageous results and outcomes that include but not limited to: (1) increased material removal rate, (2) uniform material removal with uniform machining depth, and (3) improved quality (roughness or smoothness) of machined surface.

Example 5

LAM of Bone with Analysis

Fresh bovine cadaver femur specimens were collected from a slaughterhouse. The mid-shaft portions were isolated and sectioned into approximately 100×25×20 mm blocks of cortical bone by using a commercial band saw. The specimens were placed in normal saline and cleaned with ultrasonic cleaner for an hour. The ultrasonic cleaning was followed by each 12-hour immersion cleaning cycle in the distilled water-formaldehyde solutions in volumetric proportions of 75%-25%, 50%-50%, 25%-75%, 15%-85%, 10%-90%, and 5%-95% and concluded with 12-hour immersion cleaning in 100% formaldehyde. This process removed all soft tissue and cartilage externally attached to the bone. The sample surfaces to be laser ablated were lightly ground on 800 and 1200 grit grinding papers to make surface flat and smooth (~3 μm average roughness) and cleaned with distilled water to remove any lose particles/debris before ablation. The cleaned specimens were air-blow dried for 15 minutes, sealed in plastic containers, and refrigerated until they were subjected to laser ablation procedure within 24 hours.

A continuous wave Yb-fiber coupled Nd:YAG laser with wavelength of 1070 nm was employed to carry out the laser machining trials. In order to seek understanding of fundamentals of laser-bone interaction under primary machining parameters, single isolated laser tracks were produced under each set of combination of laser machining parameters on the specimen surface. The laser beam diameter on the sample surface was 0.6 mm. The ranges of laser power, and scanning speed used in current efforts were 300-700 W and 100-250 mm/s respectively The laser fluence (F) was calculated based on the laser processing parameters employed according to this equation:

$$F = \frac{P_0 t_0}{A}$$

where $P_0$ is the input laser power, A is the cross sectional area of the laser beam, $t_0$ is the beam residence time expressed as d/V, where d is the laser beam diameter and V is the laser beam scanning speed. For above mentioned sets of laser power and scanning speed, the resultant laser fluence ranged over 3.18-8.48 J/mm$^2$ (Table 1). The machining trials were conducted in argon cover gas flown at 3 liters/min to avoid oxygen contamination on the specimen surface. The resultant values of laser fluence and beam residence time corresponding to the laser parameters employed in the present efforts are also listed in Table 2.

TABLE 2

| Laser machining parameters | | | | |
|---|---|---|---|---|
| Laser Power (W) | Scanning Speed (mm/s) | Residence Time (ms) | Remark | Laser Energy Density (J/mm$^2$) |
| 300 | 200 | 3.0 | Group 1 | 3.18 |
| 400 | 200 | 3.0 | Constant | 4.24 |
| 500 | 200 | 3.0 | Scanning Speed | 5.30 |
| 600 | 200 | 3.0 | and Variable | 6.36 |

TABLE 2-continued

Laser machining parameters

| Laser Power (W) | Scanning Speed (mm/s) | Residence Time (ms) | Remark | Laser Energy Density (J/mm²) |
|---|---|---|---|---|
| 700 | 200 | 3.0 | Power | 7.42 |
| 300 | 200 | 3.0 | Group 2 | 3.18 |
| 550 | 250 | 2.4 | Variable | 4.66 |
| 450 | 150 | 4.0 | Scanning Speed | 6.36 |
| 400 | 100 | 6.0 | and Variable Power | 8.48 |

The primary observations of machined surface for morphological features such as width, depth of machined cavity, micro cracks, and any other physical collateral thermal damage within machined surface in both top view and cross sectional view to the laser track were conducted by FEI ESEM scanning electron microscope (SEM). The SEM images were recorded electronically and measurements of morphological parameters from these images were performed digitally on a computer system using Image J™ public domain software developed at the National Institutes of Health. In order to obtain statistical variation, the measurements were conducted on 5 samples laser machined under the same set of parameters and at 5 locations in top view and in 5 cross sectional views of each sample. The elemental analysis on machined surface and interface between machined region and the base bone material was conducted using energy dispersive spectroscopy (EDS). As the depth of probe using an EDS is in the range of micron scale (0.5-3 µm, depending on the energy of the electron beam), elemental data collected using this technique provided only qualitative/semi-quantitative evaluation of change in elemental compositions within these regions due to the thermal effects during laser machining.

Figure 14:
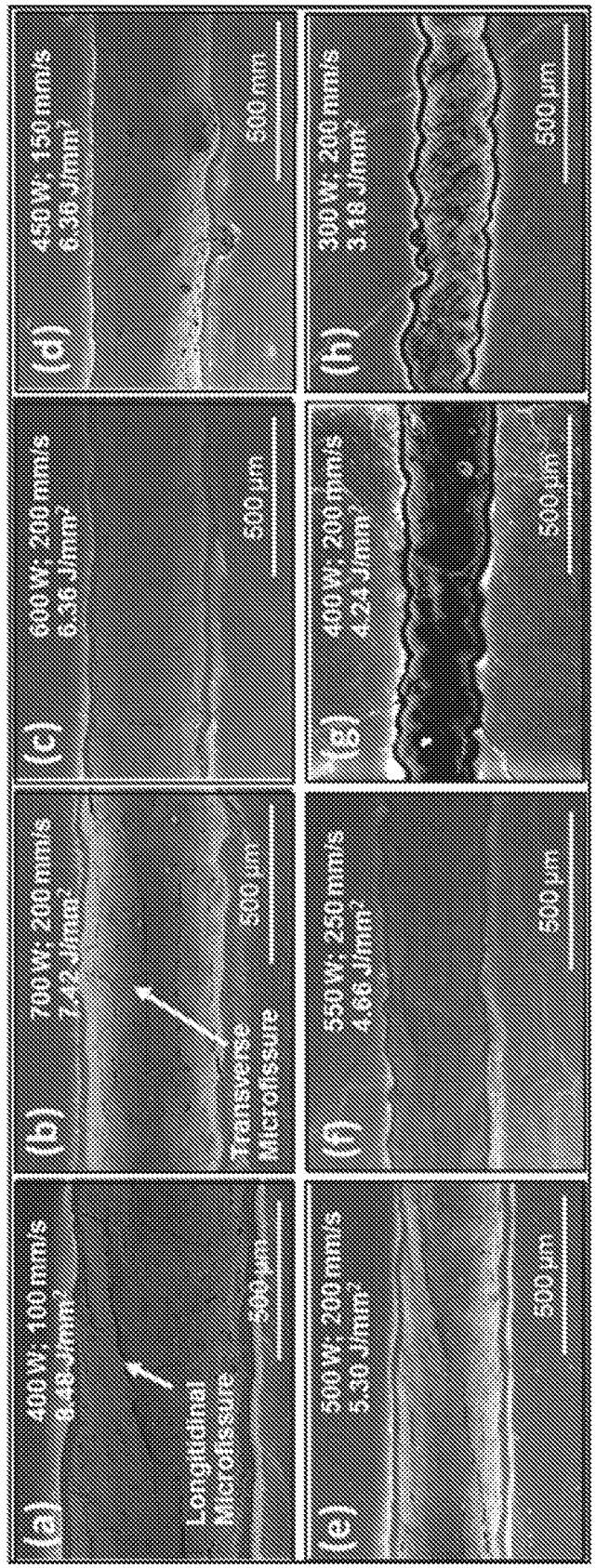
FIG. 14 shows scanning electron microscopy top view images (a)-(h) of a laser machined cavity in structural bone with various machining parameters.
Figure 15:
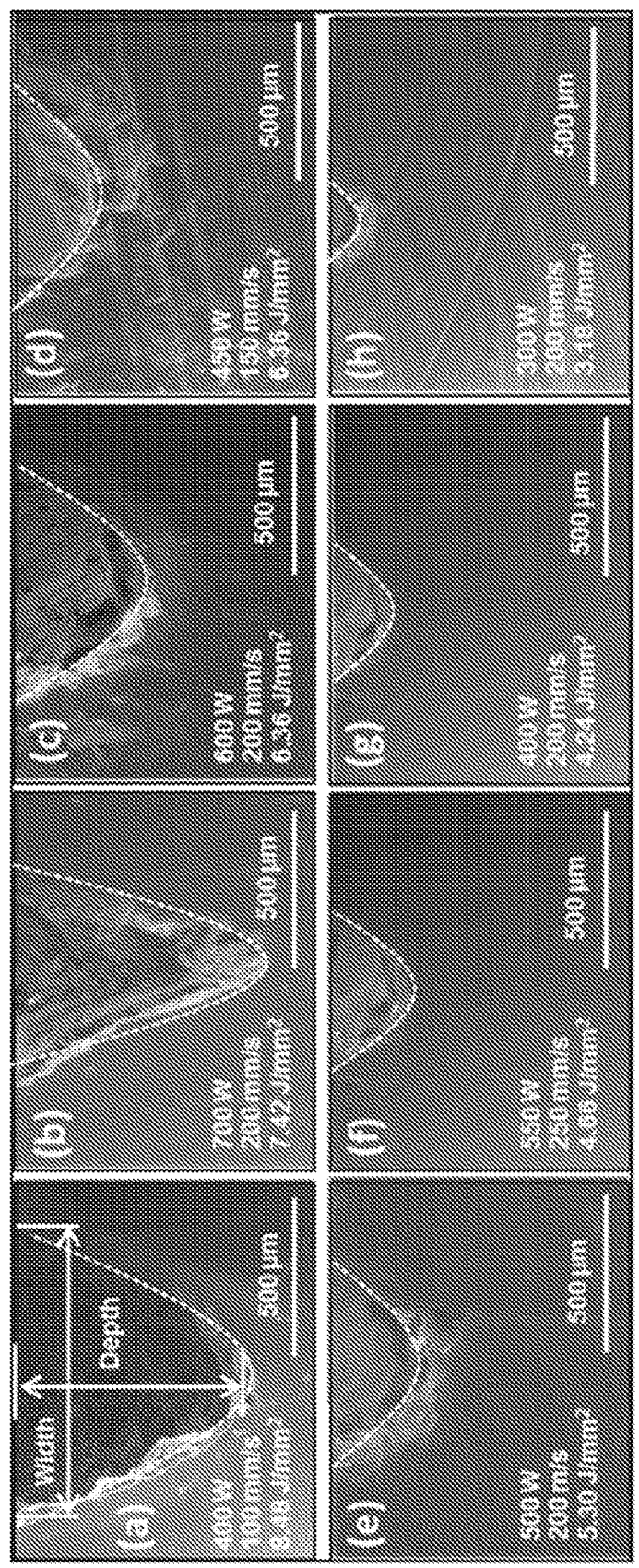
FIG. 15 shows scanning electron microscopy cross sectional view images (a)-(h) of a laser machined cavity in structural bone with various machining parameters.

SEM observations of machined bone samples in both top view and cross sectional view perpendicular to the laser track were conducted and presented in FIG. 14 and FIG. 15. Such observations revealed various physical and morphological aspects of machined cavities. The machined cavities appeared reasonably uniformly wide along the length of cavity (FIG. 14). In general, the uniformity of width along the length of machined cavity increased with increased laser input energy and lacked in any obvious effect of variation in laser scanning (machining) speed. The average geometric profile (morphology) of machined cavity in cross sectional views appeared semi-elliptical (FIG. 15). The lengths of both minor (depth) and major (width) axes of semi-elliptical machined cavity increased with increased laser input energy and again lacked in any obvious effect of variation in laser scanning (machining) speed. The presence of microfissures on the walls of machined cavity was obvious due to rapid non-isothermal laser machining process (FIG. 14). The microfissures were more visible as their physical dimensions (length and width) increased with increased laser energy input (>4.24 J/mm²). It was noteworthy that at lower laser energy input (4.24 and 3.18 J/mm²) the microfissure density (number of cracks per unit area) appeared less compared to other laser input energies and the presence of longitudinally oriented (along the length of machined track) longer and wider microfissures was predominant. On the contrary, a mesh of microfissures (oriented in longitudinal and transverse directions) existed on the surfaces of samples machined at higher laser input energy (6.36-8.48 J/mm²). Furthermore, as clearly seen in the cross sectional views of these machined cavities, these microfissures appeared shallow and confined to surface region without any deeper penetration into the bone matrix (FIG. 15).

Figure 16:
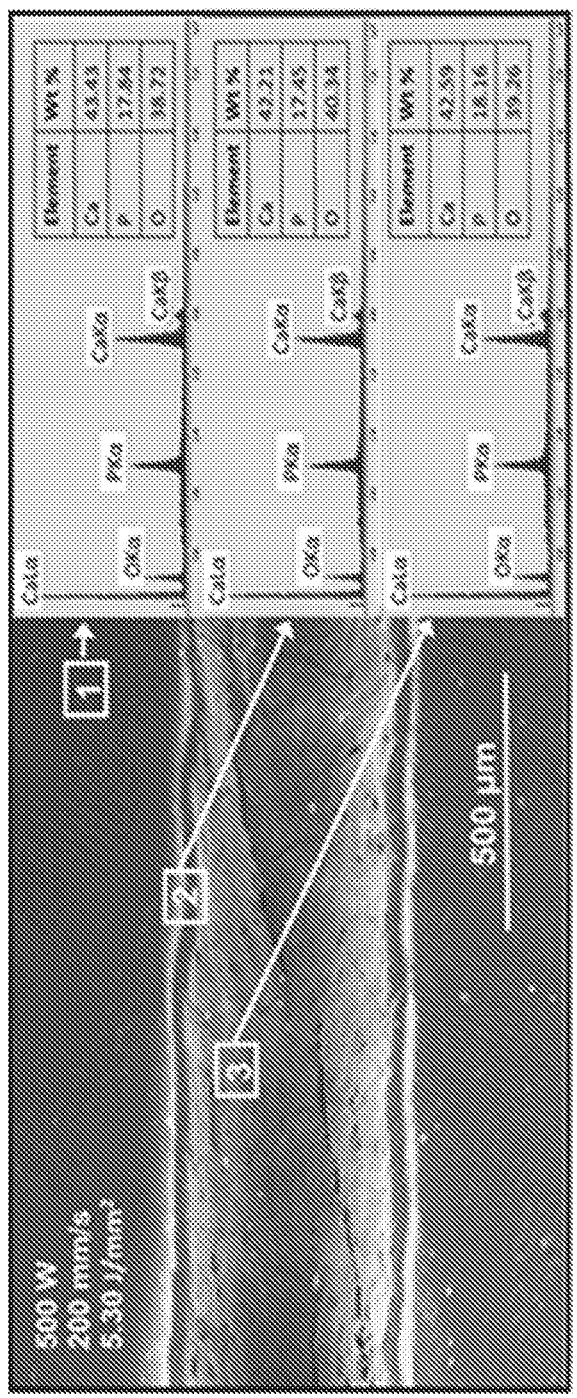
FIG. 16 shows (left) a scanning electron microscopy view of laser machined bone sample showing various machined regions 1, 2, and 3 and (right) corresponding elemental composition within machined regions 1, 2, and 3.

Even though laser based machining of bone involved non-isothermal treatment for removal of material via melting and/or vaporization at high temperature, the visual and SEM observations of machined samples in both top view and cross sectional view revealed minimal (6.36-8.48 J/mm²) or no charring (3.18-5.30 J/mm²) on machined surfaces (FIGS. 14 and 15). In almost all cases, where a light char was observed (6.3-8.49 J/mm²), it appeared to confine superficially to the surface without the possibility of further cellular damage under the machined surface. This was further confirmed with spatial (30 µm×30 µm) EDS elemental analysis on three distinct locations on the sample machined with 5.30 J/mm² (FIG. 16). These locations included location 1 on the substrate, location 2 on the interface between substrate and machined region, and location 3 on the machined surface. The analysis of all three locations provided similar elemental spectra with the presence of Ca, K, P peaks and absence of C and O peaks (FIG. 16).

Measurements of morphological aspects such as depth and width of laser machined cavities were performed on multiple digital SEM images of machined cavities in both top view and cross sectional view similar to those in FIG. 14 and FIG. 15 on a computer using Image J™ software. Further, based on the computational approach described in detail above, predictions of width and depth of cavities for the same machining parameters as those employed in the experimental efforts were made. Experimental measurements and computational predictions of the morphological features (parameters) such as width, depth, and cross sectional area of machined cavity are presented in FIG. 17. In addition, experimental as well as computational machining rates corresponding to each set of laser machining parameters (laser fluence and scanning/machining speed) derived using the equations above are also presented in FIG. 17. Although input laser energy is expected to be a prime parameter influencing the outcome of machining process, the process being a non-isothermal treatment, the thermodynamics and kinetics associated with the process are also affected by the individual machining parameters such as laser power and machining speed. In view of this and as presented in FIG. 17, the set of laser machining parameters (power and scanning speed) are combined into two distinct groups as (1) constant scanning speed with variable power and (2) variable scanning speed with variable power.

Figure 18:
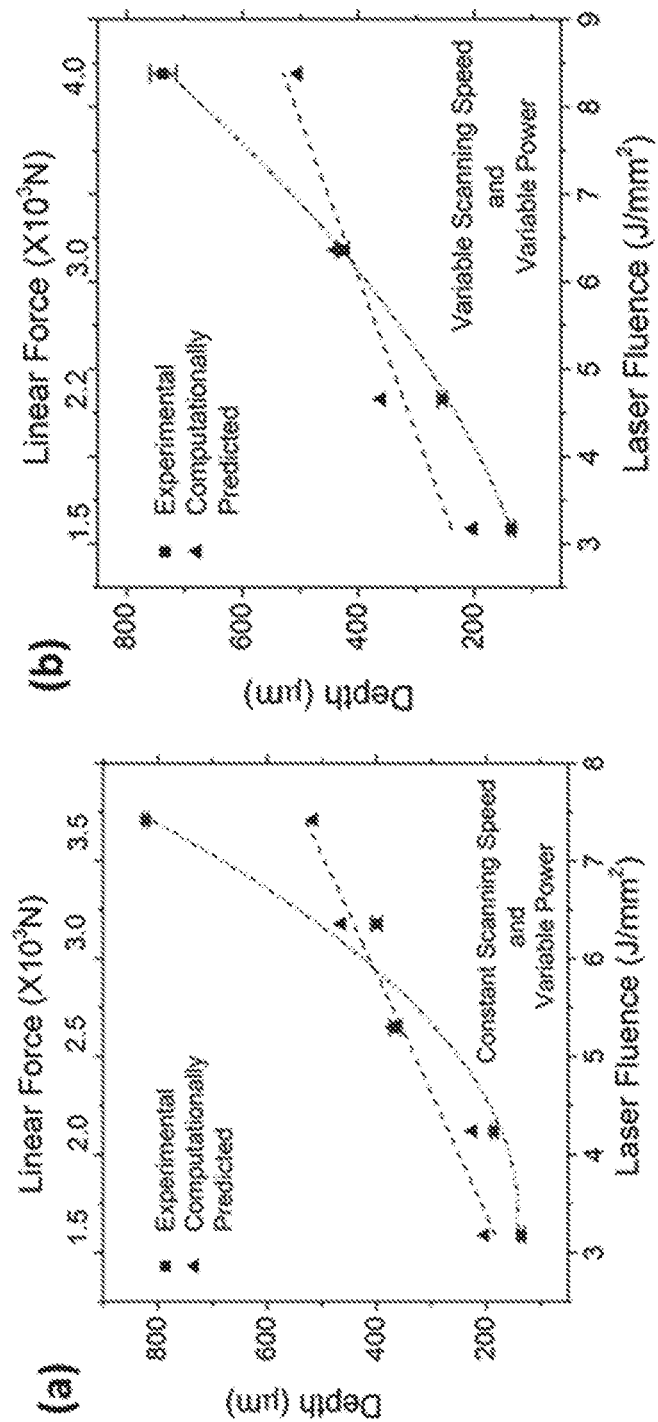
FIG. 18 shows depth of laser machined cavity in structural bone as a function of laser fluence for (a) constant scanning speed and variable power and (b) variable scanning speed and variable power.
Figure 19:
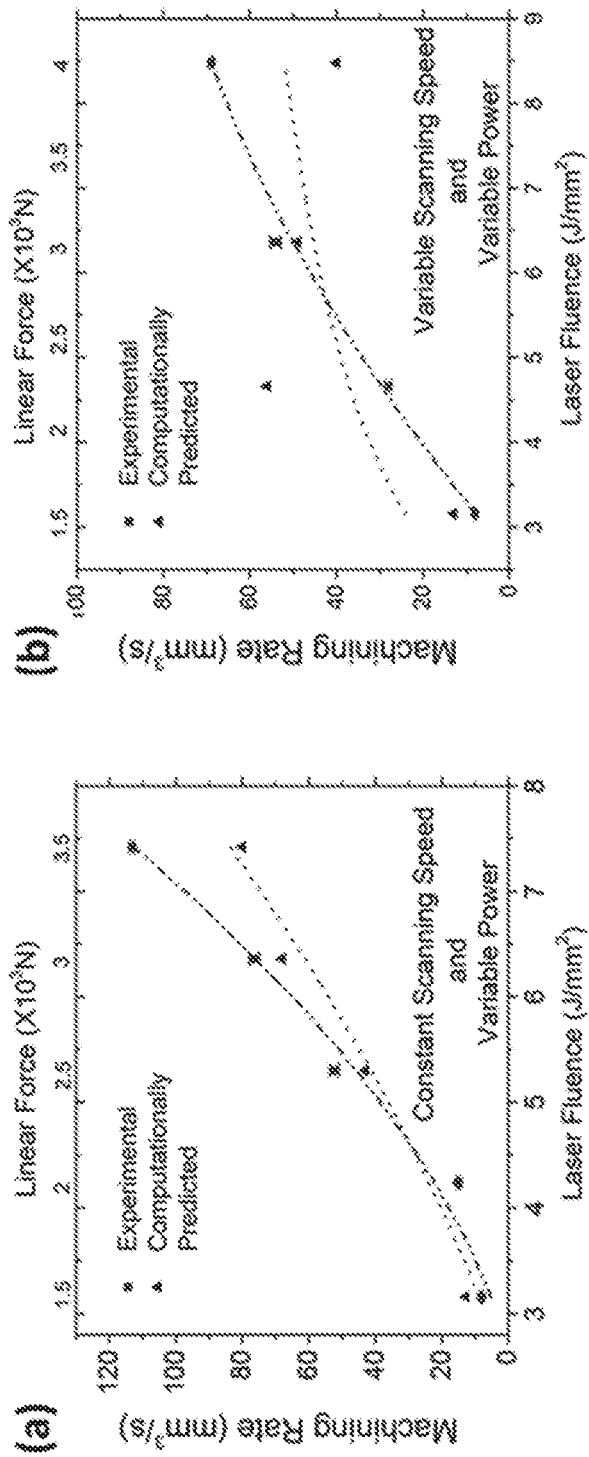
FIG. 19 shows width of laser machined cavity in structural bone as a function of laser fluence for (a) constant scanning speed and variable power and (b) variable scanning speed and variable power.

The effects of laser energy input on morphological aspects (depth and width) of machined cavity under the above mentioned two groups of laser machining parameters can be realized and compared for experimental measurements and computational predictions in FIG. 18 and FIG. 19. In general, under both groups of laser machining parameters, experimentally measured and computationally predicted depth and width increased with increased laser energy input. However, the computationally predicted values of depth are slightly higher compared to experimentally measured values and reverses the trend for the laser fluence at ~6 J/mm² (FIG. 5, FIG. 18(a) and FIG. 18(b)). On the contrary, the computationally predicted values of width remained higher than experimentally measured values over the entire range of laser fluences explored under the both groups of laser machining parameters (FIG. 17, FIG. 19(a) and FIG. 19(b)). The machining rates derived from experimental measurements and computational predictions as function of laser fluence under both group 1 and group 2 of laser machining parameters are presented in FIG. 20(a) and FIG. 20(b), respectively.

For both groups, the machining rate increased with increased laser fluence. Nonetheless, the machining rate corresponding to the experimental measurements remained lower than the computationally predicted values for the laser fluences lower than ~4.75 J/mm$^2$ for group 1 and ~5.8 J/mm$^2$ for group 2 respectively and reverses in the trend above those two laser fluences for group 1 and group 2 respectively (FIG. 17, FIG. 20(a) and FIG. 20(b)). Finally, as stated earlier, laser based machining being primarily a process of removal of material through melting and vaporization, it is highly dictated by the thermodynamics and kinetics of the process. Hence, computationally predicted time-temperature relationship is likely to provide a tool for reasonable affirmation of experimental outcome.

Figure 21:
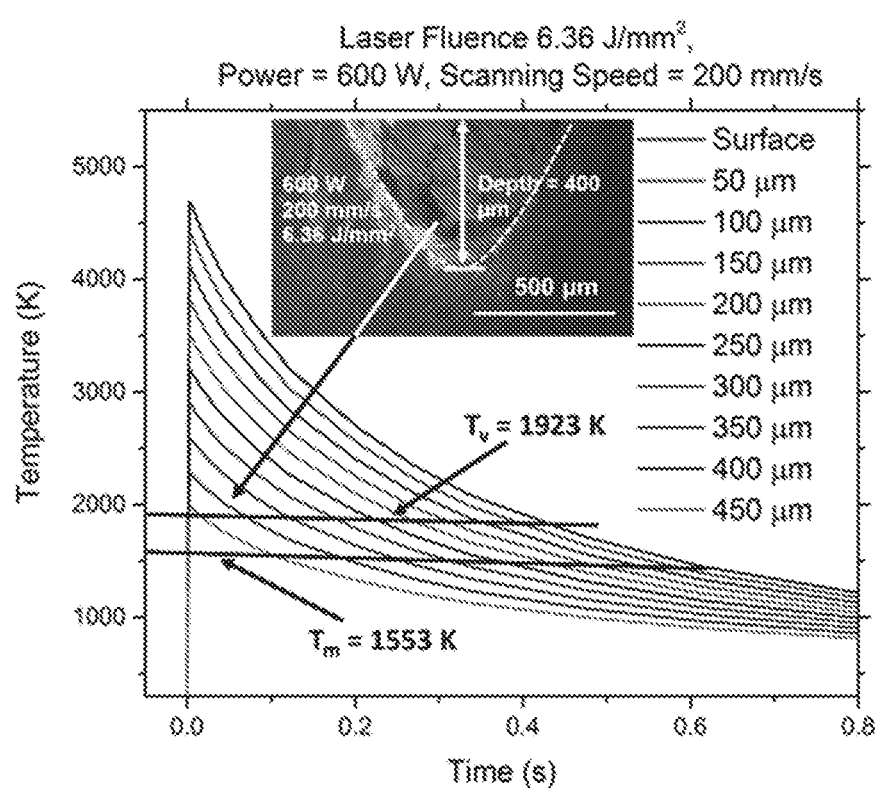
FIG. 21 shows thermal fields at various depths below surface and corresponding evolution of machined cavity in laser machined structural bone.
Figure 22:
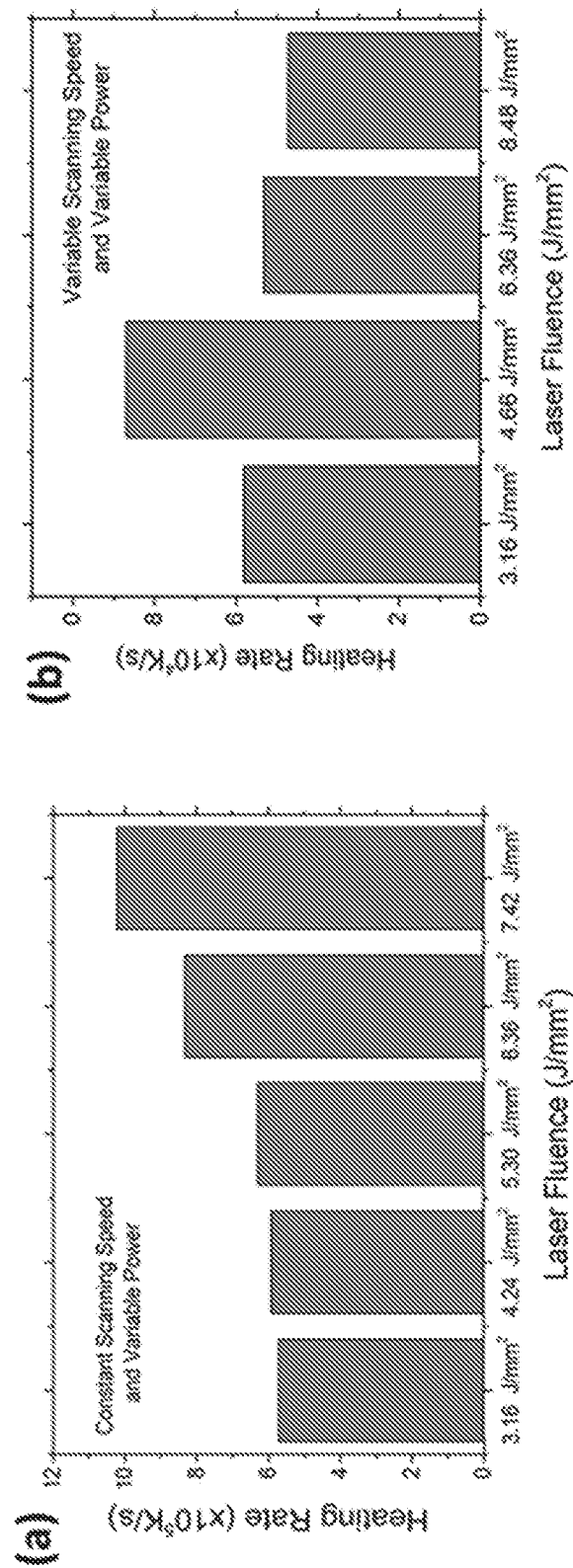
FIG. 22 shows heating rate during laser machining of structural bone as a function of laser fluence for (a) constant scanning speed and variable power and (b) variable scanning speed and variable power.
Figure 23:
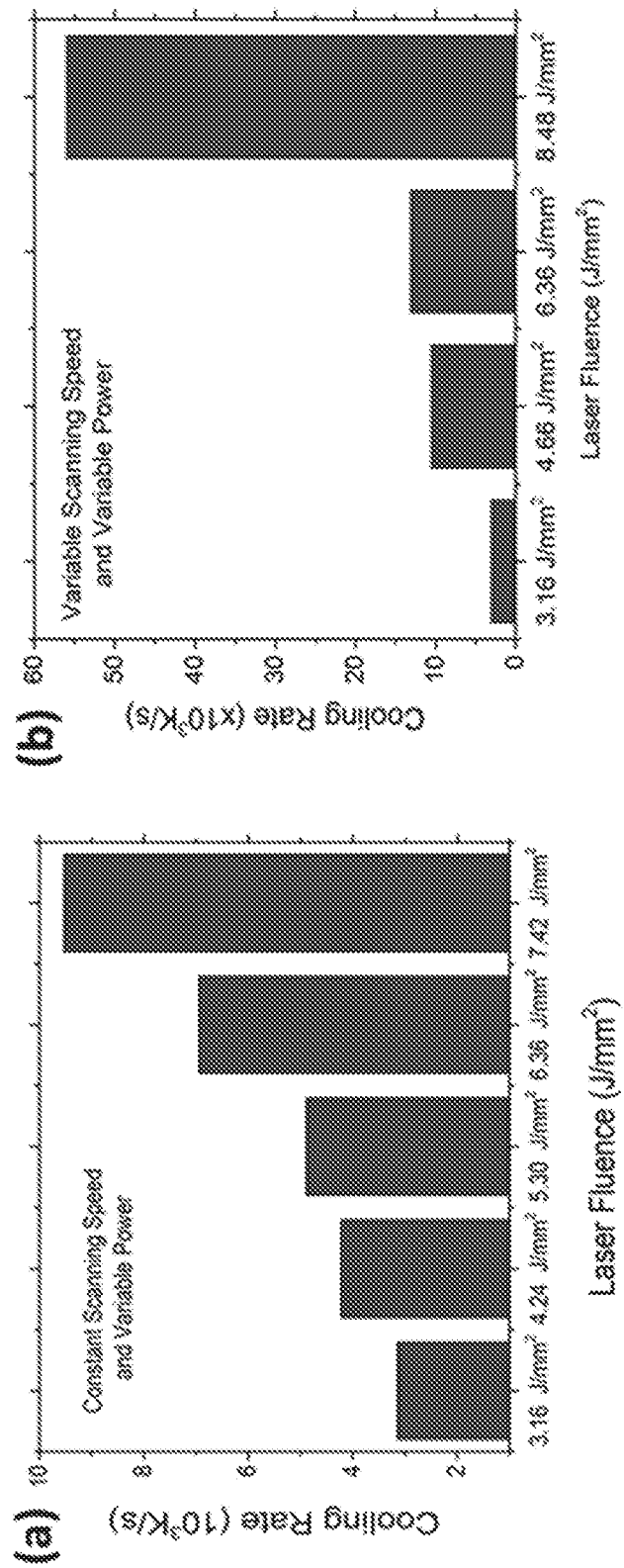
FIG. 23 shows cooling rate during laser machining of structural bone as a function of laser fluence for (a) constant scanning speed and variable power and (b) variable scanning speed and variable power.

In light of this, FIG. 21 presents computationally predicted temperature as function of time of machining at various depths from the surface of the sample machined with laser fluence of 6.36 J/mm$^2$ (600 W, 200 mm/s). The inset of the figure provides the experimentally observed cross sectional view of the machined cavity of the same sample. As can be clearly seen, most of the material within the machined cavity has been removed at and above vaporization temperature ($T_v$=1923K) to the maximum depth of ~400 μm. Similar computational predictions for temperature as function of time corresponding to all sets of processing conditions indicated the highest instantaneous temperature on the surface of the bone sample ranged between 2450K and 4750K. Accordingly, corresponding heating rates and cooling rates on the surface are presented in FIG. 22 and FIG. 23, respectively. While for group 1, heating rate increased with increase in laser fluence (FIG. 22(a)), for group 2 (FIG. 22(b)) it did not follow any specific trend for heating rate as function of laser fluence. On the contrary, even though, in both groups of processing parameters, the cooling rate increased with increase in laser fluence, the cooling rates were at the levels of 10$^3$ K/s for group 1 and 10$^4$ K/s for group 2 (FIG. 23). Furthermore, The heating rates were at the levels of 10$^5$ K/s for group 1 and 10$^4$ K/s for group 2. The heating rate is predominantly dictated by process kinetics (combination of laser fluence and machining speed) whereas cooling rate is primarily influenced by the thermophysical properties such as thermal conductivity and specific heat of the material (bone).

The reasonable closeness between experimentally observed and computationally predicted values of depth, width, and machining rate was a result of consideration during computational modeling to the combinatorial effects of multiple physical phenomena, coupling of heat transfer and fluid flow effects, phase transition and kinetics, and effects of body forces occurring during laser-bone interaction (machining). In spite of consideration to such conceivable details, the laser material-interaction being very complex and highly dynamic process, additional nonlinear temporal dynamic physical effects may occur and lead to deviation in experimental observations and computational predictions described above.

To reveal the effect of thermodynamics and kinetics on the attributes of machined cavity, as stated earlier, two groups of combinations of laser machining parameters were considered (Table 2 and FIG. 16). Group 1 consisted of constant scanning (machining) speed and variable power and group 2 consisted of variable scanning (machining) speed and variable power. In group 1, machining speed (kinetics) being constant, the effect of laser fluence (thermodynamics, temperature) can be clearly realized where as in group 2, in varying both machining speed and laser fluence, the kinetic effects of the process are evident.

The cooling rates corresponding to the highest laser fluences of 8.48 J/mm$^2$ in group 1 and 7.24 J/mm$^2$ in group 2 being highest at 5.6×10$^4$ K/s and 9.5×10$^3$ K/s respectively (FIG. 10), and low thermal conductivity of the bone material (0.4824 W/m$^2$/K, Table 1) led to formation of extensive network of microfissures on the surface (FIGS. 14(a) and 14(b)). Additionally, the formation of such microfissures can also be supplemented by the linear force generated as result of laser fluence and machining speed. As laser interaction time with the bone under the set of machining speed explored in the present study being extremely small (~milliseconds), the linear force exerted on the bone surface ranges between 1.5×10$^3$ and 4.0×10$^3$ N. Such linear forces of 4.0×10$^3$N and 3.5×10$^3$ N for laser fluences of 8.38 J/mm$^2$ and 7.42 J/mm$^2$ respectively being on the higher side of the range of linear force (FIG. 17), they contribute to formation of extensive network of surface microfissures. The intensity of such microfissures gradually reduced for the samples machined with reduced laser fluence (FIG. 14(c)-14(h)). These microfissures appeared to be very shallow in depth thereby primarily confining to the surface region (FIG. 14) without propagating deeper into the substrate material (FIG. 15). As mentioned earlier, although during machining under the set of parameters considered (Table 2) the surface temperature reached in the range of 2450K-4750K, due to extremely high heating rate (>10$^4$ K/s) followed by very high cooling rate (>10$^3$) the bone material was instantaneously ablated (machined) without the presence of any detectable carbonised layer on the machined surface (FIG. 16).

The evolution of morphology of machined cavity as function of laser machining parameters (laser fluence: power and scanning speed) can be realized through the evolution of depth and width of the cavity. Hence, the interrelationship between depth and width as function of machining parameter is expressed as a ratio of depth to width for both experimentally observed values ($R_E$) and computationally predicted values ($R_C$) and are presented in FIG. 17. The values of $R_C$ for both group 1 and group 2 of processing parameters indicate that depth is nearly twice as the width of the machined cavity and a narrow range of variation in $R_C$ (±0.02 for group 1 and ±0.025 for group 2), as mentioned earlier, is indicative of assumption that the same set of physical phenomena occur during laser-bone interaction (machining) for all set of machining parameters explored in the present study. However, $R_E$ values are true reflection of occurrence of nonlinear phenomena during machining with various combinations of parameters. Although, except for highest fluences, all other sets of machining parameters in both groups of experimentally observed values of $R_E$, continue to maintain the relationship of depth as nearly twice the width. However, $R_E$ values for higher fluences are much higher (1.19 for 7.42 J/mm$^2$ and 0.79 for 8.38 J/mm$^2$) compared to the rest of $R_E$ values in both groups driving the range of variation in $R_E$ (±0.37 for group 1 and ±0.165 for group 2) to higher levels compared to the range of variation in $R_C$. These observations, suggest that at higher fluences the dynamics of the machining was probably predominantly dominated by the key hole effect associated with highly efficient interaction of incoming laser energy with the substrate via multiple internal reflections within the evolving machining cavity. Such interaction was likely to ablate/ remove the material from the bottom of evolving cavity via several physical phenomena such as but not limited to vaporization of the material and ejection of molten material due to the back pressure of vaporized material. In the present computational modelling, although the back pressure due to vaporized material was taken into account, the intensification of laser energy via multiple internal reflection in the cavity was not accounted for due to extremely dynamic and complex nature of surface topography constantly evolving cavity surface. Such anomaly associated with higher fluences is likely to affect depth more severely than width thereby generating higher depth to width ratio (FIG. 17).

Figure 20:
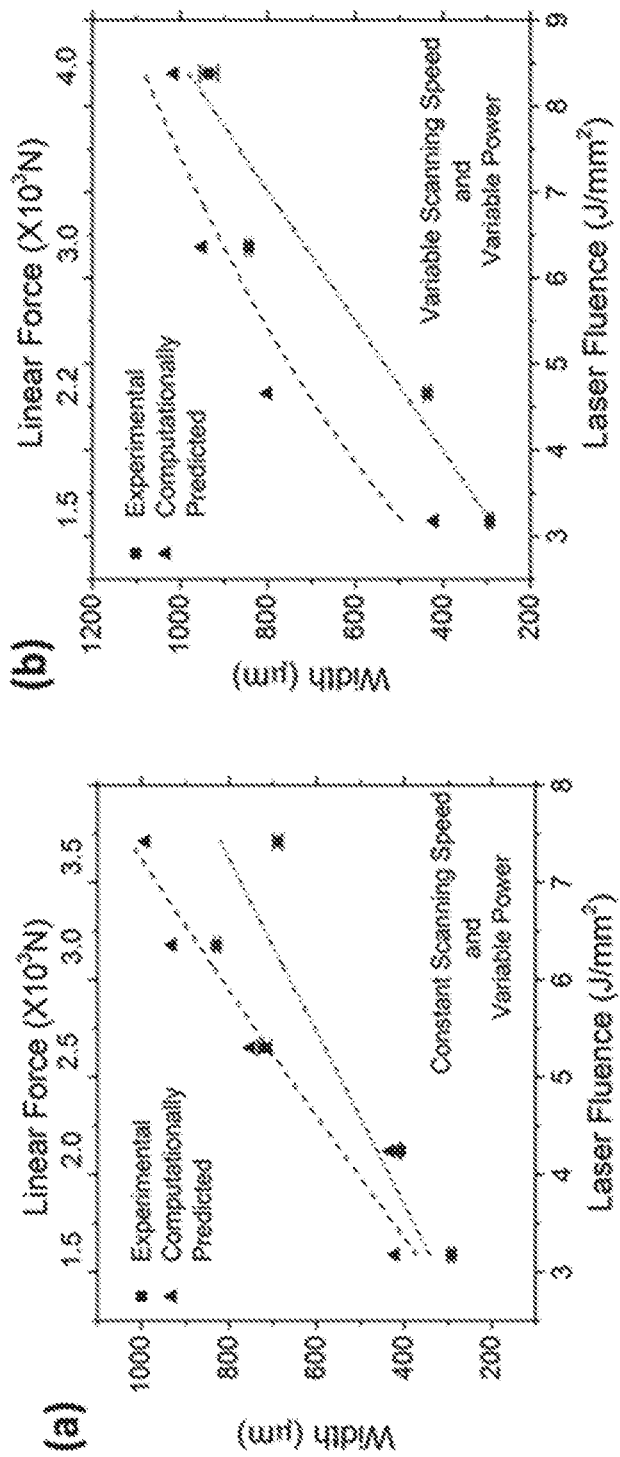
FIG. 20 shows laser machining rate of structural bone as a function of laser fluence for (a) constant scanning speed and variable power and (b) variable scanning speed and variable power.

The above explained physical phenomenon and its effect on evolution of machined cavity as function of laser machining parameter (laser fluence) can be clearly realized from FIGS. 18, 19, and 20. As the depth of machined cavity is likely to be severely affected by the internal reflection of laser beam at higher laser fluence (>6 J/mm$^2$ for both group 1 and group 2), the experimentally measured values of depth are higher than computationally predicted values (FIGS. 18(a) and 18(b)). On the contrary, as evolution of the width is surface phenomenon it was likely to be least affected by the internal reflection phenomenon over the range of laser fluences used in the present efforts (FIG. 17). The computationally predicted values of width remain higher than experimentally measured values for both group 1 and group 2 machining parameters (FIGS. 19(a) and 19(b)). Furthermore, as explained earlier, the determination of machining rate involved both depth and width, the relationship between machining rate and laser fluence for both group 1 and group 2 machining parameters followed the same trend as that for depth as function of laser fluence. At laser fluences >4.75 J/mm$^2$ for group 1 and >5.8 J/mm$^2$ for group 2, the experimentally measured values of machining rate are higher than computationally predicted values (FIGS. 20(a) and 20(b), respectively). As mentioned earlier, for improved accuracy in computationally predicted values of the machined attributes (depth, width, and machining rate), the computational model took into account several physical phenomena such as phase transfer, fluid flow, convection, surface tension, and vapor recoil pressure, body forces, emissivity along with the effect of composite nature of the bone on its resultant thermophysical properties. In spite of such approach, a reasonable gap existed between experimentally observed/ derived and computationally predicted values of the machined attributes (FIGS. 18, 19, and 20). Such gap can be attributed to the factors such as but not limited to (1) consideration of only room temperature (constant) thermophysical properties and emissivity of bone components (due to lack of temperature dependent data in the open literature), (2) inability to conceive/recognize any temporal and special effects during machining, (3) inability to recognize possible nonlinear behaviour of already considered physical phenomena during machining, and (4) spatially anisotropic and heterogeneous nature of bone structure.

Finally, it was evident that the computational model with consideration to substantial details related to physical phenomena occurring during laser based machining enabled prediction of the values of attributes of machined cavity (depth, width, and machining rate) reasonably close to the experimentally determined values and the trend in variation of relationship between these attributes as function of laser fluence. Although, the computational model under predicted the values of depth and machining rate at higher laser fluences compared to those experimentally derived, it established the validity of the approach, especially at lower laser fluences. This was further confirmed from FIG. 21 where most of the material within the machined cavity has been removed (inset of FIG. 21) at and above vaporization temperature ($T_v$=1923K) to the maximum depth of ~400 nm in about 450 ms. The computational model also identified the complexity and non-linear nature of laser interaction with bone at higher fluences.

REFERENCES CITED

The following references, to the extent that they provide exemplary procedural or other details supplementary to those set forth herein, are specifically incorporated herein by reference.

Us Patent Documents

U.S. Pat. No. 9,387,041
US Patent Publication No. 2011/0218524 A1, published on Sep. 8, 2011, with Giorgio Cattaneo listed as the inventor.

Non-Patent Literature

Parsa H K. An investigation into the temperature distribution resulting from cutting of compact bone using a reciprocating bone saw. Master of Engineering thesis, Department of Mechanical and Electronic Engineering, Institute of Technology, Sligo, Ireland, 2006.
Tetsch P. Development of raised temperature after osteotomies. Journal of Maxillofacial Surgery 1974; 2:141-145.
Plaskos C, Hodgson A J, Inkpen K, McGraw R W. Bone cutting errors in total knee arthroplasty. The Journal of Arthroplasty 2002; 17(6):698-705.
Giraud J-Y, Villemin S, Darmana R, Cahuzac J-Ph, Autefage A, Morucci J-P. Bone cutting. Clinical Physics and Physiological Measurement 1991; 12(1):1-19.
Adili A. Robot-assisted orthopedic surgery. Surgical Innovation 2004; 11(2):89-98.
Krause W R, Bradbury D W, Kelly J E, Lunceford E M. Temperature elevations in orthopaedic cutting operations. Journal of Biomechanics 1982; 15(4):267-275.
Dahotre N B, Joshi S S. Machining of Bone and Hard Tissues. Springer International, Switzerland, 2016.
Sugita N, Warisawa S, Mitsuishi M. A cutting temperature study of bone machining for orthopaedic robotic surgery 2005. In Proc. of the 20th Annual Meeting of the ASPE, pages 142-145.
Sugita N, Ishii K, Sui J, Terashima M. Multi-grooved cutting tool to reduce cutting force and temperature during bone machining. CIRP Annals-Manufacturing Technology 2014; 63(1):101-104.
Toksvig-Larsen S, Ryd L, Lindstrand A. Temperature influence in different orthopedic saw blades. The Journal of Arthroplasty 1992; 7(1):21-24.
Toksvig-Larsen S, Ryd L, Lindstrand A. On the problem of heat generation in bone cutting. Studies on the effects on liquid cooling. Journal of Bone & Joint Surgery 1991; 73(1):13-15.
Toksvig-Larsen S, Ryd L, Lindstrand A. An internally cooled saw blade for bone cuts: lower temperatures in 30 knee arthroplasties. Acta Orthopaedica 1990; 61(4):321-323.
Keaveny T M, Wachtel E F, Ford C M, Hayes W C. Differences between the tensile and compressive strengths of bovine tibial trabecular bone depend on modulus. Journal of Biomechanics 1994; 27(9):1137-1146.
Libonati F, Vergani L. Bone toughness and crack propagation: an experimental study. Procedia Engineering 2014; 74:464-467.

Peterlik H, Roschger P, Klaushofer K, Fratzl P. From brittle to ductile fracture of bone. Nature Materials 2006; 5(1): 52-55.

Plaskos C, Hodgson A J, Cinquin P. In Medical Image Computing and Computer-Assisted Intervention-MICCAI 2003; Springer, Berlin, pages 254-261.

Denis K, Van Ham G, Vander Sloten J, Van Audekercke R, Van der Perre G, De Schutter J, Kruth J P, Bellemans J, Fabry G. In International Congress Series, Elsevier, Amsterdam 2001; vol. 1230, pp. 300-306.

Romeo U, Del Vecchio A, Palata G, Tenore G, Visca P, Maggiore C. Bone damage induced by different cutting instruments: an in vitro study. Brazilian Dental Journal 2009; 20(2):162-168.

Baek K-W, Deibel W, Marinov D, Griessen M, Dard M, Bruno A, Zeilhofer H-F, Cattin P, Juergens P. A comparative investigation of bone surface after cutting with mechanical tools and Er:YAG laser. Lasers in Surgery and Medicine 2015; 47(5) 426-432.

Rode A, Gamaly E, Luther-Davies B, Taylor B, Dawes J, Chan A, Lowe R, Hannaford P. Subpicosecond laser ablation of dental enamel. Journal of Applied Physics 2002; 92(4):2153-2158.

Chan A, Rode A, Gamaly E, Luther-Davies B, Taylor B, Dawes J, Lowe M, Hannaford P. Ablation of dental enamel using subpicosecond pulsed lasers. International Congress Series (2003); 1248:117-119.

Rode A, Gamaly E, Luther-Davies B, Taylor B, Graessel M, Dawes J, Chan A, Lowe R, Hannaford P. Precision ablation of dental enamel using a subpicosecondpulsed laser. Australian Dental Journal 2003; 48(4):233-239.

Baek, K.-W, Deibel W, Marinov D, Griessen M, Bruno A, Zeilhofer H-F, Cattin Ph, Juergens Ph. Clinical applicability of robot-guided contact-free laser osteotomy in cranio-maxillo-facial surgery: in-vitro simulation and in-vivo surgery in minipig mandibles. British Journal of Oral and Maxillofacial Surgery 2015; 53(10):976-981.

Stübinger S, Nuss K, Pongratz M, Price J, Sader R, Zeilhofer H F, von Rechenberg B. Comparison of Er:YAG laser and piezoelectric osteotomy; An animal study in sheep. Laser in Surgery and Medicine 2010; 42(8):743-51.

Stübinger S, Biermeier K, Baechi B, Ferguson S J, Sader R, von Rechenberg B. Comparison of Er:YAG laser, piezoelectric, and drill osteotomy for dental implant site preparation: a biomechanical and histological analysis in sheep. Lasers in Surgery and Medicine 2010; 42(7):652-61.

Taylor R, Shklar G, Roeber F. The effects of laser radiation on teeth, dental pulp, and oral mucosa of experimental animals. Oral Surg Oral Med Oral Pathol, 1965; 19(6): 786-95.

Stock K, Diebolder R, Hausladen F, Hibst R. Efficient bone cutting with the novel diode pumped Er:Yag laser system: In vitro investigation and optimization of the treatment parameters. In SPIE BiOS, International Society for Optics and Photonics, 2014; pages 89263P-89263P.

Giraud J Y, Villemin S, Darmana R, Cahuzac J P, Autefage A, Morucci J P. Bone cutting. Clin. Phys. Physiol. 1991; Meas. 12(1):1-19.

A. Kruusing, Opt. Lasers Eng. 41(2), 307 (2004).

H. Jelínková, Lasers for Medical Applications: Diagnostics, Therapy and Surgery; Elsevier, Amsterdam, 2013.

Koechner, W., Solid-state Laser Engineering (6$^{th}$ Edition), Springer, Berlin (2005).

Willstrand, O., Intensity distribution conversion from Gaussian to Top-Hat in a single-mode fiber connector (Master's Thesis) in *Lund Reports on Atomic Physics*, (2013).

S. Rupprecht, K. Tangermann-Gerk, J. Wiltfang, F. W. Neukam, A. Schlegel, Lasers Med. Sci. 926 19(2), 81 (2004).

T. Gudra, S. Muc, Eur. Phys. J. Spec. Topics 154(1), 85 (2008).

K. M. Sasaki, A. Aoki, S. Ichinose, I. Ishikawa, Lasers Surg. Med. 31(5), 322 (2002).

J. T. Walsh, T. F. Deutsch, Lasers Surg. Med. 9(4), 327 (1989).

R. Wallace, C. Whiners, J. McGeough, A. Muir, J. Mater. Process. Technology 149(1), 557 (2004)

Gonzalez, C., Van De Merwe, W. P., Smith, M., & Reinisch, L. (1990). Comparison of the erbium-yttrium aluminum garnet and carbon dioxide lasers for in vitro bone and cartilage ablation. The Laryngoscope, 100(1), 14-17.

U. Romeo, A. Del Vecchio, G. Palata, G. Tenore, P. Visca, C. Maggiore, Braz. Dental J. 20(2), 936 162 (2009).

K. W. Baek, W. Deibel, D. Marinov, M. Griessen, M. Dard, A. Bruno, H. F. Zeilhofer, P. Cattin, 938 P. Juergens, Lasers Surg. Med. (2015).

M. Mehrwald, J. Burgner, C. Platzek, C. Feldmann, J. Raczkowsky, H. Worn, in BiOS (Inter-940 national Society for Optics and Photonics, 2010), pp. 75,620P-75,620P.

M. M. Ivanenko, T. Mitra, P. Hering, in EOS/SPIE European Biomedical Optics Week (Inter-942 national Society for Optics and Photonics, 2000), pp. 46-51.

M. Ivanenko, M. Werner, S. Afilal, M. Klasing, P. Hering, Med. Laser Appl. 20(1), 13 (2005).

M. Ivanenko, P. Hering, Appl. Phys. B 67(3), 395 (1998).

A. McKenzie, Physics in Medicine and Biology 35(9), 1175 (1990).

M. Ivanenko, P. Hering, Applied Physics B 67(3), 395 (1998)

K. Stock, R. Diebolder, F. Hausladen, R. Hibst, in SPIE BiOS (International Society for Optics and Photonics, 2014), pp. 89, 263P-89, 263P.

J. T. Walsh Jr, D. A. Hill, in Optics, Electro-Optics, and Laser Applications in Science and Engineering (International Society for Optics and Photonics, 1991), pp. 27-33.

K. Trauner, N. Nishioka, D. Patel, Am. J. Sports Med. 18(3), 316 (1990).

J. P. Winkler, A temperature study of laser-irradiated bone. PhD Thesis, University of Tennessee, USA (1997).

B. Fink, T. Schneider, S. Braunstein, G. Schmielau, W. Rüther, Arthroscopy: J. Arthrosc. Relat. Surg. 12(2), 217 (1996).

I. M. Stubig, P. A. Reder, G. Facer, H. G. Rylander, A. J. Welch, in OE/LASE '93: Optics, Electro-956 Optics, & Laser Applications in Science& Engineering (International Society for Optics and Photonics, 1993), pp. 10-16.

L. R. Friesen, C. M. Cobb, J. W. Rapley, L. Forgas-Brockman, P. Spencer, J. Periodontol. 70(1), 959 75 (1999).

Y. M. Lee, R. Tu, A. Chiang, Y. C. Huang, J. Biomed. Opt. 12(6), 060505 (2007).

Youn, P. Sweet, G. M. Peavy, Lasers Surg. Med. 39(4), 332 (2007).

J. S. Nelson, A. Orenstein, L. H. L. Liaw, M. W. Berns, Lasers Surg. Med. 9(4), 362 (1989).

R. J. O'Donnell, T. F. Deutsch, T. J. Flotte, C. A. Lorente, W. W. Tomford, H. J. Mankin, K. T. Schomacker, J. Orthopaedic Res. 14(1), 108 (1996).

K. M. Sasaki, A. Aoki, S. Ichinose, I. Ishikawa, Lasers in Surgery and Medicine 31(5), 322 (2002)

A. Pourzarandian, H. Watanabe, A. Aoki, S. Ichinose, K. M. Sasaki, H. Nitta, I. Ishikawa, 966 Photomed. Laser Therapy 22(4), 342 (2004).

E. D. A. de Mello, R. M. Pagnoncelli, E. Munin, M. Sant, Ana Filho, G. P. S. de Mello, E. A. L. Arisawa, M. G. de Oliveira, Lasers Surg. Med. 23(3), 253 (2008).

U. K. Akyol, M. Güngörmüs, C. Gündogdu, H. Erdem, J Contemp. Dent p. 2 (2009).

H. Pretel, R. Lizarelli, L. Ramalho et al., Lasers Surg. Med. 39(10), 788 (2007).

J. T. Payne, G. M. Peavy, L. Reinisch, D. C. Van Sickle, Lasers Surg. Med. 29(1), 38 (2001).

Clayman L, Fuller T, Beckman H. Healing of continuous-wave and rapid superpulsed, carbon dioxide, laser-induced bone defects. J Oral Surg, 1978; 36:932-7.

Small I A, Osborn T P, Fuller T, et al. Observations of carbon dioxide laser and bone bur in the osteotomy of the rabbit tibia. J Oral Surg, 1979; 37:159-66.

Ivanenko M M, Fahimi-Weber S, Mitra T, et al. Bone tissue ablation with sub-microS pulses of a Q-switch CO(2) laser: histological examination of thermal side effects. Lasers Med Sci, 2002; 17:258-64.

Charlton A, Dickinson M R, King T A, et al. Erbium-YAG and holmiumYAG laser ablation of bone. Lasers Med Sci 1990; 5:365-73.

Buchelt M, Kutschera H P, Katterschafka T, et al. Erb:YAG and Hol:YAG laser osteotomy: the effect of laser ablation on bone healing. Lasers Surg Med, 1994; 15:373-81.

Devlin H, Dickinson M, Freemont A J, et al. Healing of bone defects prepared using the Erbium-YAG laser. Lasers Med Sci 1994; 9:239-42.

Narendra B. Dahotre and Sameehan S. Joshi, Machining of Bone and Hard Tissues, Springer International Publishing, AG Switzerland, 2016.

M. Sussman, P. Smereka, S. Osher, A level set approach for computing solutions to incompressible two-phase flow, Journal of Computational Physics. 114 (1994) 146-159.

What is claimed is:

1. A method of laser-assisted cutting, shaping, and machining of bone, comprising the steps of:
   (a) determining a target bone volume to be machined;
   (b) predicting isotherms corresponding to interfaces between a solid substrate/melting zone and a melting zone/vaporized region using a Multiphysics computational model to define a predicted morphology of the target bone region;
   (c) scanning a laser beam along a surface area axis of the target bone region using an assigned laser track to produce the predicted morphology of the target bone region; and
   (d) ejecting a bone residue from the target bone region creating a machined void in the bone corresponding to the predicted morphology of the target bone region,
   wherein the laser track is assigned a heat flux boundary with a moving laser beam defined by the equation:

$$-k\left[\left(\frac{\partial T}{\partial x}\right)+\left(\frac{\partial T}{\partial y}\right)+\left(\frac{\partial T}{\partial z}\right)\right]=P_X+h[T-T_0]+\varepsilon\sigma[T^4-T_0^4]$$

wherein k is thermal conductivity, h is heat transfer coefficient, $\varepsilon$ is emissivity, $\sigma$ is Stefan-Boltzman constant, T is temperature, $T_0$ is ambient temperature, x is an X-coordinate in a three dimensional space, y is a Y-coordinate in a three dimensional space, z is a Z-coordinate in a three dimensional space, and $P_X$ is an input laser power intensity distribution.

2. The method of claim 1, wherein $P_X$ is $P_g$ or $P_{th}$ or $P_{db}$, wherein $P_g$ is a three dimensional Gaussian laser beam power intensity distribution, $P_{th}$ is a top hat laser beam power intensity distribution, and $P_{db}$ is a dumbbell laser beam power intensity distribution.

3. The method of claim 2, wherein $P_g$, $P_{th}$, and $P_{db}$ are defined by the equations:

$$P_g = \frac{P_0}{\pi r_0^2}\exp^{-\left[\frac{x^2+y^2}{r_0^2}\right]^2},$$

$$P_{th} = \frac{P_0}{\pi r_0^2}\exp^{-\left[\frac{x^2+y^2}{r_0^2}\right]^2}, \text{ where}$$

$n \infty$, and $$P_{db} = \frac{2P_0}{\pi r_0^2}\left(\frac{x}{r_0}\right)^2\exp^{-\left[\frac{x^2+y^2}{r_0^2}\right]^2},$$

where $P_0$ is laser input power and $r_0$ is radius of beam at which laser power transverse intensity decreases to $$\frac{1}{e^2}.$$

4. The method of claim 1, further comprising the step of: choosing a laser to generate a laser beam having a wavelength in the range of 300 nm to 29,400 nm.

5. The method of claim 1, further comprising the step of: choosing a laser that is a Ti-Sapphire laser, a $CO_2$ laser, an Excimer laser, a Er-YAG laser, a copper vapor laser, a Yb-fiber laser, or a combination thereof.

6. The method of claim 1, further comprising the step of: choosing a laser to generate the laser beam to have a focal spot of 0.3-3 mm diameter.

7. The method of claim 1, further comprising the step of: choosing a laser to operate in pulsed mode or continuous mode to produce the laser beam.

8. The method of claim 1, further comprising the step of: setting a residence time of a laser generating the laser beam to be in the range of 0.5 µs-4 ms.

9. An apparatus for laser-assisted cutting, shaping, and machining of bone, comprising:
   (a) a laser source capable of delivering a laser beam to a bone target;
   (b) a dynamic focusing unit for delivering the laser beam to a visualized target site; and
   (c) a real time controller (RTC) capable of simultaneous processing of visualized target site data and controlling the laser source and controlling the dynamic focusing unit,
   wherein the RTC is able to correct laser source output and assign a laser beam track to prevent heat affected zones in the bone target and to cut/shape/machine a target bone region to have a predicted morphology, wherein the predicted morphology is defined by predicting isotherms corresponding to interfaces between a solid substrate/melting zone and a melting zone/vaporized region using a Multiphysics computational model, and wherein the laser track is assigned a heat flux boundary with a moving laser beam defined by the equation:

$$-k\left[\left(\frac{\partial T}{\partial x}\right)+\left(\frac{\partial T}{\partial y}\right)+\left(\frac{\partial T}{\partial z}\right)\right]=P_X+h[T-T_0]+\varepsilon\sigma[T^4-T_0^4]$$

wherein k is thermal conductivity, h is heat transfer coefficient, ε is emissivity, σ is Stefan-Boltzman constant, T is temperature, $T_0$ is ambient temperature, x is an X-coordinate in a three dimensional space, y is a Y-coordinate in a three dimensional space, z is a Z-coordinate in a three dimensional space, and $P_X$ is an input laser power intensity distribution.

10. The apparatus of claim 9, wherein $P_X$ is $P_g$ or $P_{th}$ or $P_{db}$, wherein $P_g$ is a three dimensional Gaussian laser beam power intensity distribution, $P_{th}$ is a top hat laser beam power intensity distribution, and $P_{db}$ is a dumbbell laser beam power intensity distribution.

11. The apparatus of claim 10, wherein $P_g$, $P_{th}$, and $P_{db}$ are defined by the equations:

$$P_g = \frac{P_0}{\pi r_0^2} \exp^{-\left[\frac{x^2+y^2}{r_0^2}\right]^2},$$

$$P_{th} = \frac{P_0}{\pi r_0^2} \exp^{-\left[\frac{x^2+y^2}{r_0^2}\right]^2}, \text{ where}$$

$n \infty$, and $$P_{db} = \frac{2P_0}{\pi r_0^2}\left(\frac{x}{r_0}\right)^2 \exp^{-\left[\frac{x^2+y^2}{r_0^2}\right]^2},$$

where $P_0$ is laser input power and $r_0$ is radius of beam at which laser power transverse intensity decreases to $$\frac{1}{e^2}.$$

12. The apparatus of claim 9, wherein the laser source generates a laser beam having a wavelength in the range of 300 nm to 29,400 nm.

13. The apparatus of claim 9, wherein the laser source is a Ti-Sapphire laser, a $CO_2$ laser, an Excimer laser, a Er-YAG laser, a copper vapor laser, a Yb-fiber laser, or a combination thereof.

14. The apparatus of claim 9, wherein the laser source generates a laser beam having a focal spot of 0.3-3 mm diameter.

15. The apparatus of claim 9, wherein the laser source can be operated in pulsed mode or continuous mode to produce the laser beam.

16. The apparatus of claim 9, wherein the residence time of the laser source generating the laser beam to be in the range of 0.5 μs-4 ms.

17. A method of laser-assisted cutting, shaping, and machining of bone, comprising the steps of:
(a) determining a target bone volume to be machined;
(b) predicting isotherms corresponding to interfaces between a solid substrate/melting zone and a melting zone/vaporized region using a Multiphysics computational model to define a predicted morphology of the target bone region;
(c) scanning a laser beam along a surface area axis of the target bone region using an assigned laser track to produce the predicted morphology of the target bone region; and
(d) ejecting a bone residue from the target bone region creating a machined void in the bone corresponding to the predicted morphology of the target bone region, wherein the laser track is assigned a heat flux boundary with a moving laser beam defined by the equation:

$$-k\left[\left(\frac{\partial T}{\partial x}\right)+\left(\frac{\partial T}{\partial y}\right)+\left(\frac{\partial T}{\partial z}\right)\right] = -P_g + h[T-T_0] + \varepsilon\sigma[T^4 - T_0^4]$$

wherein k is thermal conductivity, h is heat transfer coefficient, ε is emissivity, σ is Stefan-Boltzman constant, T is temperature, $T_0$ is ambient temperature, x is an X-coordinate in a three dimensional space, y is a Y-coordinate in a three dimensional space, z is a Z-coordinate in a three dimensional space, and $P_g$ is a three-dimensional Gaussian laser beam distribution.

18. The method of claim 17, wherein $P_g$ is defined by the equation:

$$P_z = (P/(\frac{\pi}{4}D^2))\exp\left(-\frac{(x-V_{in}*t)^2}{(2\phi^2)}\right)$$

where P is laser power, x is distance along an X-axis, D is diameter of a laser beam, and ϕ is a standard deviation of laser beam intensity.

19. The method of claim 17, further comprising the step of: choosing a laser to generate a laser beam having a wavelength of 1070 nm.

20. The method of claim 17, further comprising the step of choosing a laser that is a continuous wave Yb-fiber coupled Nd:YAG laser.

21. The method of claim 17, further comprising the step of choosing a laser to operate at a laser power of 300 W to 700 W.

22. The method of claim 17, further comprising the step of choosing a laser to have a machining speed of 110 mm/s to 250 mm/s.

23. The method of claim 17, further comprising the step of choosing a laser to have a laser fluence of 3.18 J/mm² to 8.48 J/mm².

24. An apparatus for laser-assisted cutting, shaping, and machining of bone, comprising:
(a) a laser source capable of delivering a laser beam to a bone target;
(b) a dynamic focusing unit for delivering the laser beam to a visualized target site; and
(c) a real time controller (RTC) capable of simultaneous processing of visualized target site data and controlling the laser source and controlling the dynamic focusing unit,
wherein the RTC is able to correct laser source output and assign a laser beam track to prevent heat affected zones in the bone target and to cut/shape/machine a target bone region to have a predicted morphology, wherein the predicted morphology is defined by predicting isotherms corresponding to interfaces between a solid substrate/melting zone and a melting zone/vaporized region using a Multiphysics computational model, and wherein the laser track is assigned a heat flux boundary with a moving laser beam defined by the equation:

$$-k\left[\left(\frac{\partial T}{\partial x}\right)+\left(\frac{\partial T}{\partial y}\right)+\left(\frac{\partial T}{\partial z}\right)\right] = -P_g + h[T-T_0] + \varepsilon\sigma[T^4 - T_0^4]$$

wherein k is thermal conductivity, h is heat transfer coefficient, ε is emissivity, σ is Stefan-Boltzman constant, T is temperature, $T_0$ is ambient temperature, x is an X-coordinate in a three dimensional space, y is a Y-coordinate in a three dimensional space, z is a Z-coordinate in a three dimensional space, and $P_g$ is a three-dimensional Gaussian laser beam distribution.

25. The apparatus of claim 24, wherein $P_g$ is defined by the equation:

$$P_z = \left(P / \left(\frac{\pi}{4}D^2\right)\right)\exp\left(-\frac{(x - V_{in}*t)^2}{(2\phi^2)}\right)$$

where P is laser power, x is distance along an X-axis, D is diameter of a laser beam, and ϕ is a standard deviation of laser beam intensity.

26. The apparatus of claim 24, wherein the laser source generates a laser beam having a wavelength of 1070 nm.

27. The apparatus of claim 24, wherein the laser source is a continuous wave Yb-fiber coupled Nd:YAG laser.

28. The apparatus of claim 24, wherein the laser source generates a laser beam having a laser power of 300 W to 700 W.

* * * * *

UNITED STATES PATENT AND TRADEMARK OFFICE
CERTIFICATE OF CORRECTION

PATENT NO. : 10,729,497 B2  
APPLICATION NO. : 16/310917  
DATED : August 4, 2020  
INVENTOR(S) : Narendra Dahotre et al.

Page 1 of 2

It is certified that error appears in the above-identified patent and that said Letters Patent is hereby corrected as shown below:

In the Specification

In Column 9, Line 58, delete "c is" and insert -- $\varepsilon$ is --, therefor.
In Column 10, Lines 9-11, delete "$$P_{db} = \frac{P_0}{\pi r_0^2}\left(\frac{x}{r_0}\right)^2 \exp^{-\left[\frac{x^2+y^2}{r_0^2}\right]^2}$$" and insert $$P_{db} = \frac{2P_0}{\pi\, r_0^2}\left(\frac{x}{r_0}\right)^2 exp^{-\left[\frac{x^2+y^2}{r_0^2}\right]^2}$$

-- --, therefor.
In Column 30, Line 1, delete "~400 nm" and insert -- ~400 µm --, therefor.

Signed and Sealed this  
Twenty-fourth Day of August, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,729,497 B2

In the Claims

In Column 34, Lines 11-12, in Claim 3, delete "$P_{th} = \frac{P_0}{\pi r_0^2} \exp{-\left[\frac{x^2+y^2}{r_0^2}\right]^2}$,"

and insert --$P_{th} = \frac{P_0}{\pi r_0^2} exp{-\left[\frac{x^2+y^2}{r_0^2}\right]^n}$,-- therefor.

In Column 35, Lines 20-22, in Claim 11, delete "$P_{th} = \frac{P_0}{\pi r_0^2} \exp{-\left[\frac{x^2+y^2}{r_0^2}\right]^2}$,"

and insert --$P_{th} = \frac{P_0}{\pi r_0^2} exp{-\left[\frac{x^2+y^2}{r_0^2}\right]^n}$,-- therefor.

In Column 35, Line 24, in Claim 11, delete "n ∞, and" and insert -- n → ∞ --, and --, therefor.